United States Patent [19]
Urion et al.

[11] Patent Number: 5,566,680
[45] Date of Patent: Oct. 22, 1996

[54] TRANSDUCER-TIPPED INTRAUTERINE PRESSURE CATHETER SYSTEM

[75] Inventors: Kenard E. Urion, Woodbury, N.J.; George R. Allen, Grand Island, N.Y.; Brian T. O'Mara, Mercerville, N.J.

[73] Assignee: Graphic Controls Corporation, Buffalo, N.Y.

[21] Appl. No.: 532,438

[22] Filed: Sep. 22, 1995

[51] Int. Cl.$^6$ .......................................... A61B 5/03
[52] U.S. Cl. ..................... 128/778; 128/775; 128/748
[58] Field of Search ...................... 128/642, 778, 128/692, 748, 772, 774, 775, 673

[56] References Cited

U.S. PATENT DOCUMENTS

| | | |
|---|---|---|
| 3,217,245 | 11/1965 | Ingmanson . |
| 3,827,428 | 8/1974 | Hon et al. . |
| 4,176,315 | 11/1979 | Sunnarborg . |
| 4,191,193 | 3/1980 | Seo . |
| 4,252,131 | 2/1981 | Hon et al. . |
| 4,274,423 | 6/1981 | Mizuno et al. . |
| 4,356,610 | 11/1982 | Hon et al. . |
| 4,456,013 | 6/1984 | De Rossi et al. . |
| 4,543,965 | 10/1985 | Pack et al. . |
| 4,610,256 | 9/1986 | Wallace . |
| 4,644,957 | 2/1987 | Ricciardelli et al. . |
| 4,658,651 | 4/1987 | Le . |
| 4,672,306 | 6/1987 | Thong . |
| 4,712,566 | 12/1987 | Hok . |
| 4,722,348 | 2/1988 | Ligtenberg et al. . |
| 4,722,730 | 2/1988 | Levy et al. . |
| 4,785,822 | 11/1988 | Wallace . |
| 4,809,704 | 3/1989 | Sogawa et al. . |
| 4,873,986 | 10/1989 | Wallace . |
| 4,901,735 | 2/1990 | von Berg . |
| 4,944,307 | 7/1990 | Hon et al. . |
| 4,966,161 | 10/1990 | Wallace et al. . |
| 4,986,671 | 1/1991 | Sun et al. . |
| 5,025,787 | 6/1991 | Sutherland et al. . |

(List continued on next page.)

OTHER PUBLICATIONS

Product packaging for the INTRAN PLUS™ device of Utah Medical Products, Inc. (copyright 1990).
Product packaging for the HP 13995 A device of Hewlett–Packard Company (copyright 1990).
Product packaging for the SENSORTIP™ device of Corometrics Medical Systems, Inc. (distributed 1987).
A. Sciscione et al., "Placental Abruption Following Placement of Disposable Intrauterine Pressure Transducer System," American Journal of Perinatology, vol. 10, No. 1 (Jan. 1993).
"Pressure Sensor Device Data," Motorcola, Inc. (2nd ed. Jan. 1994).
Advertisement for "Catheters Designed with Antiseptic Surface," Arrow International (1994).

*Primary Examiner*—William E. Kamm
*Assistant Examiner*—Seth M. Getrow
*Attorney, Agent, or Firm*—Ratner & Prestia

[57] ABSTRACT

A transducer-tipped intrauterine pressure catheter system for measuring, and delivering to an external monitor a signal representative of, the pressure in the uterus of a woman in labor. The system has a disposable catheter with an affixed asymmetric tip. A disposable, slotted, C-shaped introducer engages and positions the catheter. A reusable monitor cable has a second connector (which engages a first connector on the end of the catheter) on one end and a monitor connector (which engages the monitor) on its opposite end; the monitor cable transmits electrical signals from the first connector to the monitor. A test member is proximate the monitor connector on the monitor cable. The test member includes test circuitry assuring that the monitor cable, the second connector, and the monitor connector are operational. The test member also includes circuitry to "zero" the system. The system may also have a disposable luer fitting engaging the amnio lumen of the catheter and providing direct communication, through the amnio lumen, into the uterus. The luer fitting allows fluid samples to be withdrawn from, and fluids to be infused into, the uterus. An anti-bacterial coating may be bonded to the catheter, the tip affixed to the catheter, and the introducer.

44 Claims, 15 Drawing Sheets

U.S. PATENT DOCUMENTS

| | | |
|---|---|---|
| 5,046,965 | 9/1991 | Neese et al. . |
| 5,050,297 | 9/1991 | Metzger . |
| 5,067,491 | 11/1991 | Taylor, II et al. . |
| 5,113,868 | 5/1992 | Wise et al. . |
| 5,184,619 | 2/1993 | Austin . |
| 5,236,374 | 8/1993 | Leonard et al. . |
| 5,238,424 | 8/1993 | Vindum . |
| 5,269,311 | 12/1993 | Kirchner et al. . |
| 5,279,308 | 1/1994 | DiSabito et al. . |
| 5,313,957 | 5/1994 | Little . |
| 5,405,269 | 4/1995 | Stupecky . |
| 5,487,377 | 1/1996 | Smith et al. . |

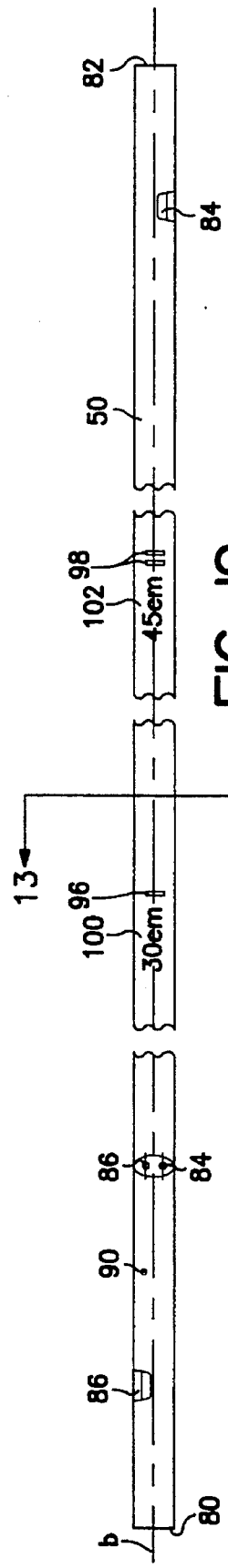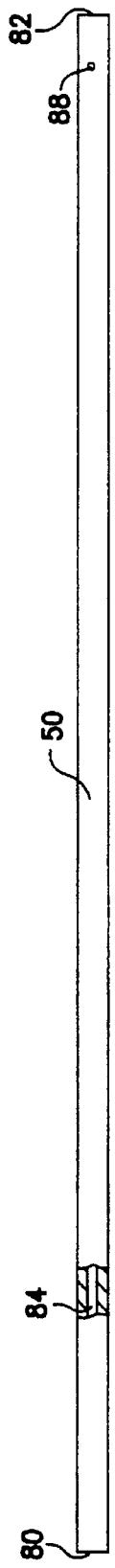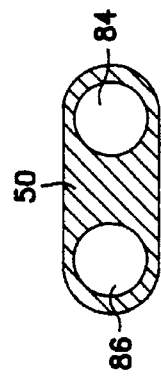

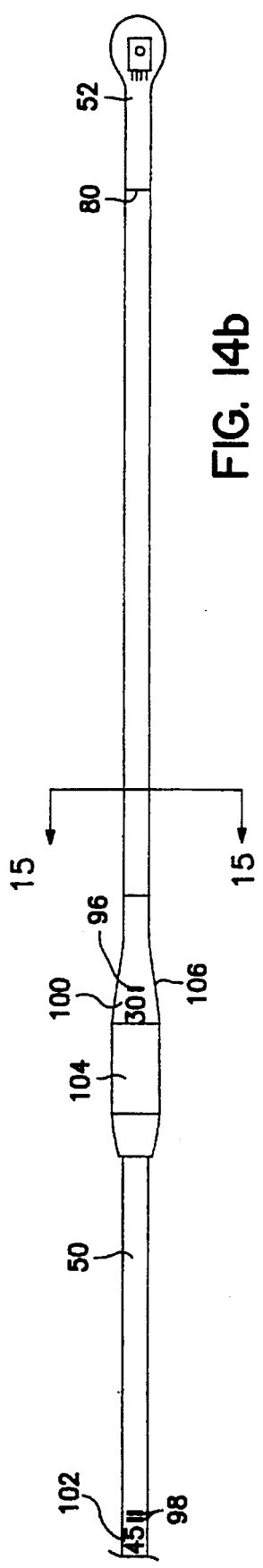
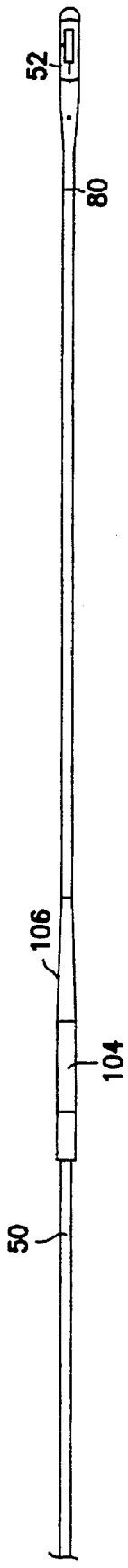
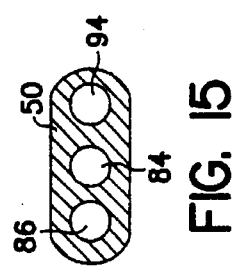
FIG. 14b
FIG. 14a
FIG. 15

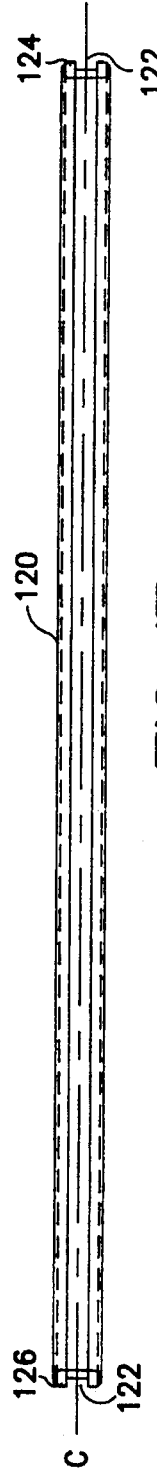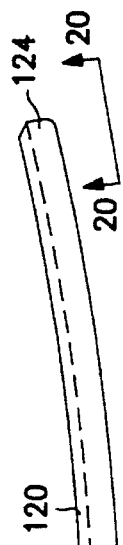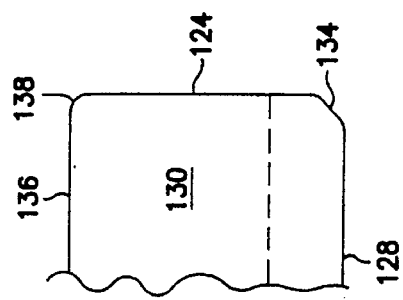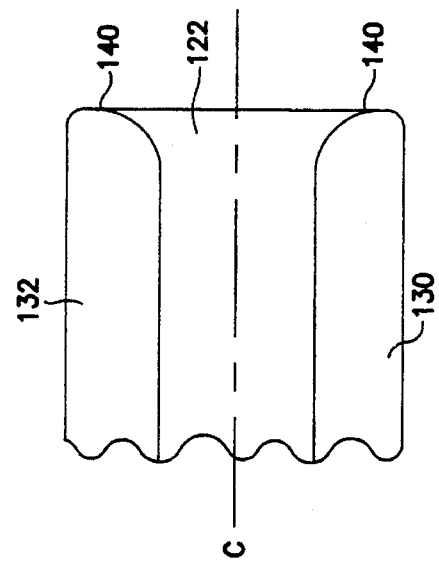
FIG. 17
FIG. 18
FIG. 19
FIG. 20

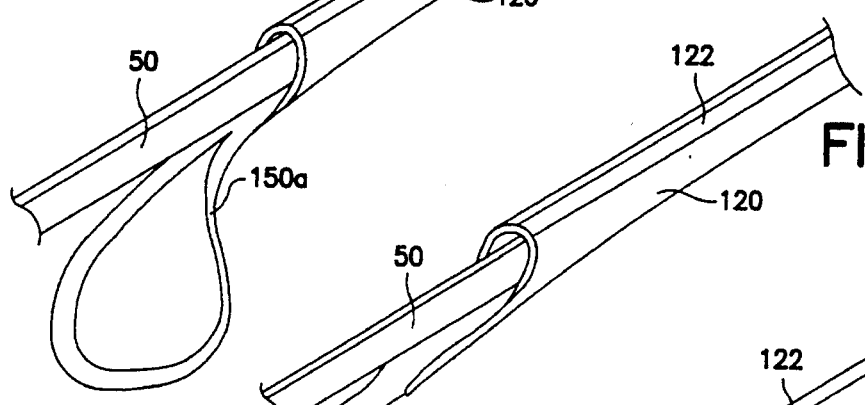
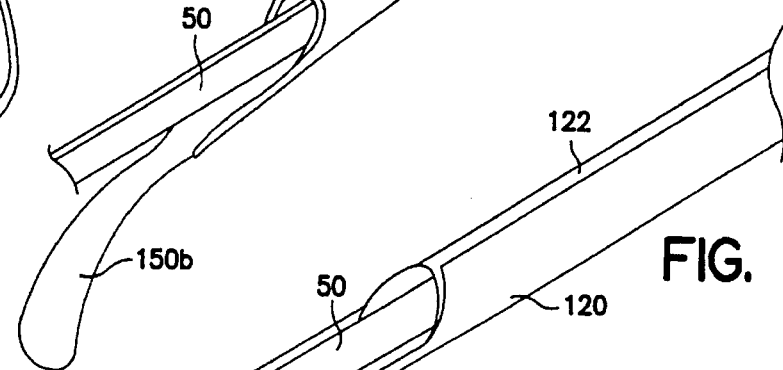
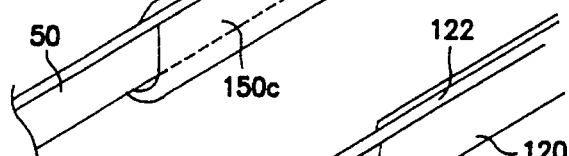
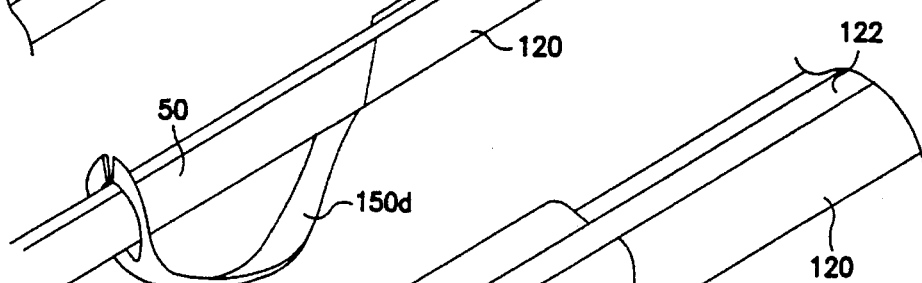
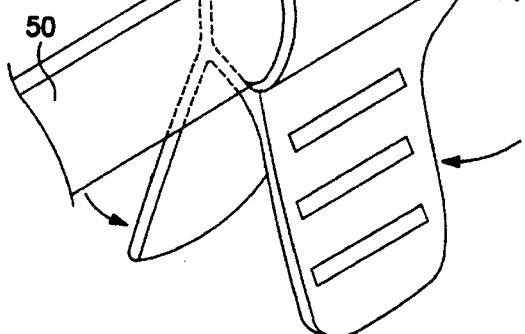

TRANSDUCER-TIPPED INTRAUTERINE PRESSURE CATHETER SYSTEM

FIELD OF THE INVENTION

This invention relates to devices used to measure pressures within a body cavity and, more particularly, to an intrauterine pressure catheter system having a pressure transducer in the catheter tip to directly and continuously measure and monitor uterine pressure during labor and childbirth.

BACKGROUND OF THE INVENTION

The procedure of monitoring and analyzing uterine contractions, during both pregnancy and labor, yields significant information concerning the condition of the fetus as well as the advancement of labor. Such a procedure is useful both during routine pregnancies and especially during difficult pregnancies, those which have increased risk to the health of the fetus, to systematically evaluate fetal stress. The procedure is also used when labor is induced. Information indicating fetal distress during pregnancy, labor, and delivery will prompt remedial action, including caesarean delivery, which may save the fetus from harm and even death. Thus, contraction frequency, duration, intensity, and resting tone are now monitored as part of accepted, standard, obstetrical procedure.

The fetal monitors widely used to monitor the uterine activity of pregnant women, as well as the condition of the fetus while in the uterus, are typically quite sophisticated. Examples of currently available fetal monitors include the FetaScan from International Biomedics, Inc.; the Corometrics 115; and the Hewlett-Packard 8040A. Regardless of their sophistication, however, fetal monitors require a device or element to actually sense the uterine contractions.

One example of such a sensing element is a tocodynamometer or tocotransducer. Tocodynamometers can sense uterine activity externally and non-invasively. The advantages offered by those devices have caused them to be widely used with fetal monitors. Tocodynamometers measure the hardness of the abdominal wall, which is an indication of uterine activity, through various mechanical elements. The tocodynamometer is held adjacent to the patient's abdomen, usually by a belt-like device, in the vicinity of the fundus (the top of the uterus). The tocodynamometer is initialized by setting the recording level so that it is about 10–15 mmHg between contractions. The output of the device is transmitted to the fetal monitor through a pressure transducer, the transducer converting the pressure change information received from the tocodynamometer to an electrical signal which it delivers to the fetal monitor.

Externally applied devices like tocodynamometers can often provide sufficient information to enable a physician to treat the mother and child during labor and delivery. Such devices may suffer large measurement errors in some cases, however, particularly when the environment has extraneous noise or the mother moves extensively. Therefore, a physician may want to have more accurate measurements than can be obtained using external monitoring devices—especially in those childbirth cases involving a risk of complication.

To obtain more reliable and accurate information about the mother's uterine contractions, a physician will often invoke intrauterine pressure monitoring. Intrauterine devices provide information about the frequency, duration, intensity, and resting tone of the uterine contractions. More important, intrauterine devices reduce measurement errors relative to external devices because the uterine pressure is measured directly.

One of the most widely used intrauterine devices is an open-ended, liquid-filled catheter. The catheter is inserted into the uterus so that the force of the uterine contractions can be transmitted through the uterine fluids and the sterile liquid solution in the catheter to an external pressure-measuring element such as a pressure transducer, strain gauge, or the like. A cumbersome procedure is required to fill the catheter with liquid and then to couple the catheter to the pressure-measuring element to complete a liquid path or column from the uterus to the transducer. A relatively long length of liquid-filled tubing must travel over the mother to the pressure-measuring element. The pressure-measuring element is connected to a monitor. Typical monitor devices include cathode ray tube displays, digital displays, recording machines, printers, and plotters.

In addition to the proper set-up of the liquid-filled catheter, the catheter must be primed with a sterile solution so that any air bubbles within the catheter are removed and a continuous liquid column is provided from the external pressure-measuring element to the tip of the catheter within the uterus. One of the disadvantages of the liquid-filled catheter is the time required to fill and prime the catheter. Particularly in critical situations, this procedure wastes valuable time. In addition, an air bubble or biologic debris will enter the open end of the catheter occasionally and compromise pressure measurements. This necessitates another time-consuming procedure: the catheter must be flushed with sterile solution to remove the air bubble or debris. Sometimes, the catheter must be replaced altogether.

Recently, disposable intrauterine pressure catheters have been introduced which place a miniature transducer in the catheter tip. The product packaging for the competitive products of Utah Medical Products, Inc. (the INTRAN PLUS™ device), Hewlett-Packard Company (the HP 13995A device), and Corometrics Medical Systems, Inc. (the SENSORTIP™ device) all describe such devices. Typically, most of these devices have relatively large tips and are supported by stiffening inserts which may damage the fetus and uterine walls. In addition, the insertion of the large tip may push bacteria high into the uterus where it is more likely to cause infection.

U.S. Pat. No. 4,944,307 issued to Hon et al. discloses an open-ended, liquid-filled catheter with an external pressure transducer. The patent criticizes transducer-tipped intrauterine pressure catheters as costly and a departure from the tried and true apparatus for measuring contractions. Nevertheless, the '307 patent recognizes the need to zero the device while in place in the uterus and provides structure to do so. Such structure may enable an open-ended, liquid-filled catheter to be zeroed during use; it is inapplicable for a transducer-tipped intrauterine pressure catheter.

U.S. Pat. No. 4,966,161 issued to Wallace et al. also discloses a catheter (although not liquid-filled) with an external pressure transducer. The transducer is located in a connector which includes a slide valve used to zero the transducer and monitor. The backside (non-uterus) of the transducer diaphragm is continuously vented to atmospheric pressure. With the valve in the "monitor" position, the transducer communicates with the fluid in the uterus through a lumen in the catheter and the uterus side of the transducer diaphragm "sees" the uterine pressure. With the valve in the "zero" position, however, a barrier prevents fluid communication between the uterus and the transducer while the uterus side of the transducer diaphragm is vented to atmospheric pressure. Because both sides of the transducer diaphragm "see" atmospheric pressure, any offset caused by the electric components of the transducer can be detected and corrected by the monitor. The structure used to zero the transducer and monitor is positioned on the disposable connector to which the catheter is attached.

As stated above, the Hewlett-Packard Company markets a transducer-tipped intrauterine pressure catheter (the HP 13995A device). It may be gathered from the instructions for use published by Hewlett-Packard for the device that the zero setting is realized before introducing the catheter as long as its measuring tip is exposed to ambient atmospheric pressure. The instructions explain that renewed zero setting is not required once the measuring tip is in situ. In fact, the instructions for Hewlett-Packard's 13995A intrauterine pressure catheter state: "Caution: Do not rezero the monitor once the catheter is inserted." Thus, the device does not provide any way to zero either the monitor or the pressure transducer after insertion (although the device can be zeroed before use).

The assertion that renewed zero setting is not required once the measuring tip is in situ is true only as long as the system does not experience any disturbances. If the monitor should fail during a measurement, which may last several hours, then a new zero setting is indispensable. Failure may occur, for example, when the main cable of the monitor is inadvertently disconnected when connecting another instrument to the monitor. Accordingly, it is desirable to provide the system with the ability to zero the system in situ.

U.S. Pat. No. 4,901,735 issued to von Berg discloses a transducer-tipped intrauterine pressure catheter which admits a reference pressure to the tip to zero the transducer while in situ. The sensor tip is surrounded by an inflatable balloon which, when deflated, acts as a diaphragm over the sensor tip pressure measuring connection. Thus, the balloon covers the transducer connection which measures uterine pressure and acts as a pressure-transmitting membrane. The reference connection of the transducer is exposed to atmospheric pressure via an air passage. To zero the transducer, a syringe filled with air forces air into the air passage, thereby inflating the balloon. Both sides of the transducer, surrounded by the air-filled balloon, now "see" the uniform air pressure prevailing inside the balloon. Therefore, the monitor should show a relative pressure of zero value. When the syringe is removed, the pressure in the balloon drops until it again engages the surface of the sensor and acts as a pressure-transmitting membrane.

The device disclosed by the '735 patent relies heavily on the loose-fitting balloon to function as a pressure-transmitting membrane. Moreover, additional, complex structures including the balloon, a syringe, and a syringe coupling are required to zero the device. All of these structures are positioned on the disposable catheter. Finally, the risk that contaminated air might get into the uterus also arises with such a device.

As stated above, Corometrics Medical Systems, Inc. markets a transducer-tipped intrauterine pressure catheter (the SENSORTIP™ device). It may be gathered from the instructions for use published by Corometrics for the device that the zero setting is realized in a manner similar to that disclosed in the '735 patent. The user is provided with a "1 cc zeroing syringe" and Corometrics' device includes a balloon and a syringe coupling (or "zero port"). To zero or rezero at any time that verification of the baseline is necessary, the user is instructed to fill the syringe with air, attach the syringe to the syringe coupling, and inject the air into the syringe coupling. The user must verify that the balloon remains inflated then zero the monitor after allowing it to stabilize. Having zeroed the device, the user is instructed to remove the syringe.

The '735 patent also suggests a second way to zero the transducer in situ. The output of the pressure transducer in situ can be compared with a representative reference value. The patent suggests that a computer might calculate a simulated reference pressure value. The reference pressure value may then be compared for zero setting with the actual pressure value measured.

As stated above, Utah Medical Products, Inc. markets a transducer-tipped intrauterine pressure catheter (the INTRAN PLUS™ device). The connector on the end of the disposable catheter has a zero slide valve with an "open" and a "closed" position. When the valve is in the "closed" position, the signal from the pressure transducer travels to the monitor and produces a reading. When the valve is in the "open" position, the signal is cut so that the monitor "sees" a null or zero output voltage. The monitor can then be adjusted, if necessary, to produce a zero reading.

U.S. Pat. No. 4,873,986 issued to Wallace discloses a transducer-tipped intrauterine pressure catheter. (The application which issued as the '986 patent was a continuation-in-part of the application which issued as U.S. Pat. No. 4,785,822; the '822 patent, in turn, refers to U.S. Pat. No. 4,610,256.) The '986 patent addresses the problem of zero balancing the transducer to ensure that the "static" readings it produces are accurate. More specifically, the '986 patent states that the device does not require rezeroing or balancing after the transducer has been inserted inside the uterus. Thus, in situ zeroing is not contemplated. The transducer has a vent channel on the backside of the diaphragm to atmospheric pressure. The opposite (uterus) side of the diaphragm "sees" the pressure in the uterus. The '986 patent discloses that the vent channel can be used to calibrate (distinguish zero) the semiconductor transducer directly using a known pressure source, even when the transducer is inside the uterus.

It is possible to zero a transducer-tipped intrauterine catheter system after insertion simply by removing the catheter from the uterus, thereby exposing both sides of the transducer diaphragm to atmospheric pressure. This introduces another inconvenient and time-consuming procedural step, however, and is undesirable because the catheter tip would no longer be sterile—inceasing the risk of infection.

To overcome the shortcomings of the existing devices for sensing uterine activity and transmitting information to a fetal monitor, an improved intrauterine pressure catheter system is provided. The general object of the present invention is to make the physician's job easier while meeting the patient's needs. It is another object to provide an apparatus for intracavity pressure monitoring that does not require a liquid column to couple the intracavity pressure to a pressure transducer. A related object is to avoid the complexity of running a liquid-filled tube from the catheter to an external pressure transducer. An important object of the present invention is, therefore, to provide an intracavity pressure device in which the pressure transducer is placed directly in the body cavity. Still another object of the present invention is to provide for continuous, accurate measurement of intrauterine contraction pressures during labor and delivery.

Yet another object of the present invention is to increase patient comfort by, among other things, reducing the number of adjustments necessary to assure optimum performance of the monitoring system. A related object is to provide an improved intrauterine pressure catheter system which has a catheter tip profile designed for patient comfort, easy insertion, and assured positioning without slippage. Another object is to provide a system that reduces the risk of infection or contamination during use.

Still another object of the present invention is to permit the monitor to be conveniently zeroed whenever it is desired to do so. The ability to test the electronic components of the system is another object. Yet another object of this invention is to provide an intrauterine device which allows fluid samples to be withdrawn from, and fluids to be infused into, the uterus.

SUMMARY OF THE INVENTION

To achieve these and other objects, and in view of its purposes, the present invention provides an intrauterine pressure catheter system for measuring intrauterine pressure and delivering a signal representative of the pressure in the uterus of a woman in labor to an external monitor. The system has a disposable, firm, flexible, flat catheter with a first end, a second end, a hollow cable lumen longitudinally traversing the inside of the catheter from the first end to the second end with a vent hole emanating from the cable lumen proximate the second end of the catheter, and a hollow amnio lumen longitudinally traversing the inside of the catheter from the first end to the second end with at least one amnio port emanating from the amnio lumen proximate the first end of the catheter. An asymmetric tip is affixed to the first end of the catheter with an undercut resisting slippage of the catheter following insertion into the uterus. The tip has a width greater than its height and tapers to an apex opposite the first end of the catheter.

An introducer engages and positions the catheter. The introducer has a bottom with a thickness and a longitudinal slot disposed along the entire length of the bottom, a top with a thickness greater than the thickness of the bottom, and a pair of side walls each with a thickness that transitions between the thickness of the top and the thickness of the bottom. The introducer defines a C-shaped cross section.

The system also includes a pressure sensor fixed and rigidly mounted in the tip affixed to the catheter. The pressure sensor measures the intrauterine pressure. A female connector socket is affixed to the second end of the catheter. A leadwire cable carried in the cable lumen of the catheter electrically connects the pressure sensor to the female connector socket. Finally, the system has a monitor cable transmitting electrical signals from the female connector socket to the monitor. The monitor cable includes a first end, a second end, a male connector plug on the first end of the monitor cable adapted to engage the female connector socket, a monitor pin connector on the second end of the monitor cable adapted to engage the monitor, and a test member proximate the monitor pin connector on the monitor cable.

The test member includes female terminals adapted to engage the male connector plug and test circuitry adapted to assure that the monitor cable, the male connector plug, and the monitor pin connector are operational. The test member also includes zero circuitry with a zero switch having a first position directing the electrical signal from the sensor to the monitor and a second position forming a voltage divider network with two resistors. A push button actuates the zero switch.

The system may also have a disposable luer fitting engaging the amnio lumen of the catheter and providing direct communication, through the amnio lumen, into the uterus. The luer fitting allows fluid samples to be withdrawn from, and fluids to be infused into, the uterus. An anti-bacterial coating may be bonded to the catheter, the tip affixed to the catheter, and the introducer.

It is to be understood that both the foregoing general description and the following detailed description are exemplary, but are not restrictive, of the invention.

BRIEF DESCRIPTION OF THE DRAWING

The invention is best understood from the following detailed description when read in connection with the accompanying drawing, in which:

FIG. 12a is a top view of the catheter in accordance with the present invention;

FIG. 12b a view of one side of the catheter shown in FIG. 12a;

FIG. 12c is a view of the side of the catheter shown in FIG. 12a opposite the side shown in FIG. 12b;

FIG. 13 is a cross-sectional view taken along the line 13—13 of FIG. 12a;

FIG. 14a is a side view of a second embodiment of the catheter in accordance with the present invention;

FIG. 14b is a top view of the embodiment of the catheter shown in FIG. 14a;

FIG. 15 is a cross-sectional view taken along the line 15—15 of FIG. 14b;

FIG. 17 is a top view of the introducer in accordance with the present invention;

FIG. 18 is a side view of the introducer shown in FIG. 17;

FIG. 19 is an enlarged view of the front end of the introducer shown in FIGS. 17 and 18;

FIG. 20 is a bottom view taken along the line 20—20 of FIG. 18;

FIGS. 22a, 22b, 22c, 22d, 22e, 22f, and 22g illustrate alternative embodiments for the grip on the introducer in accordance with the present invention;

DETAILED DESCRIPTION OF THE INVENTION

Figure 1:
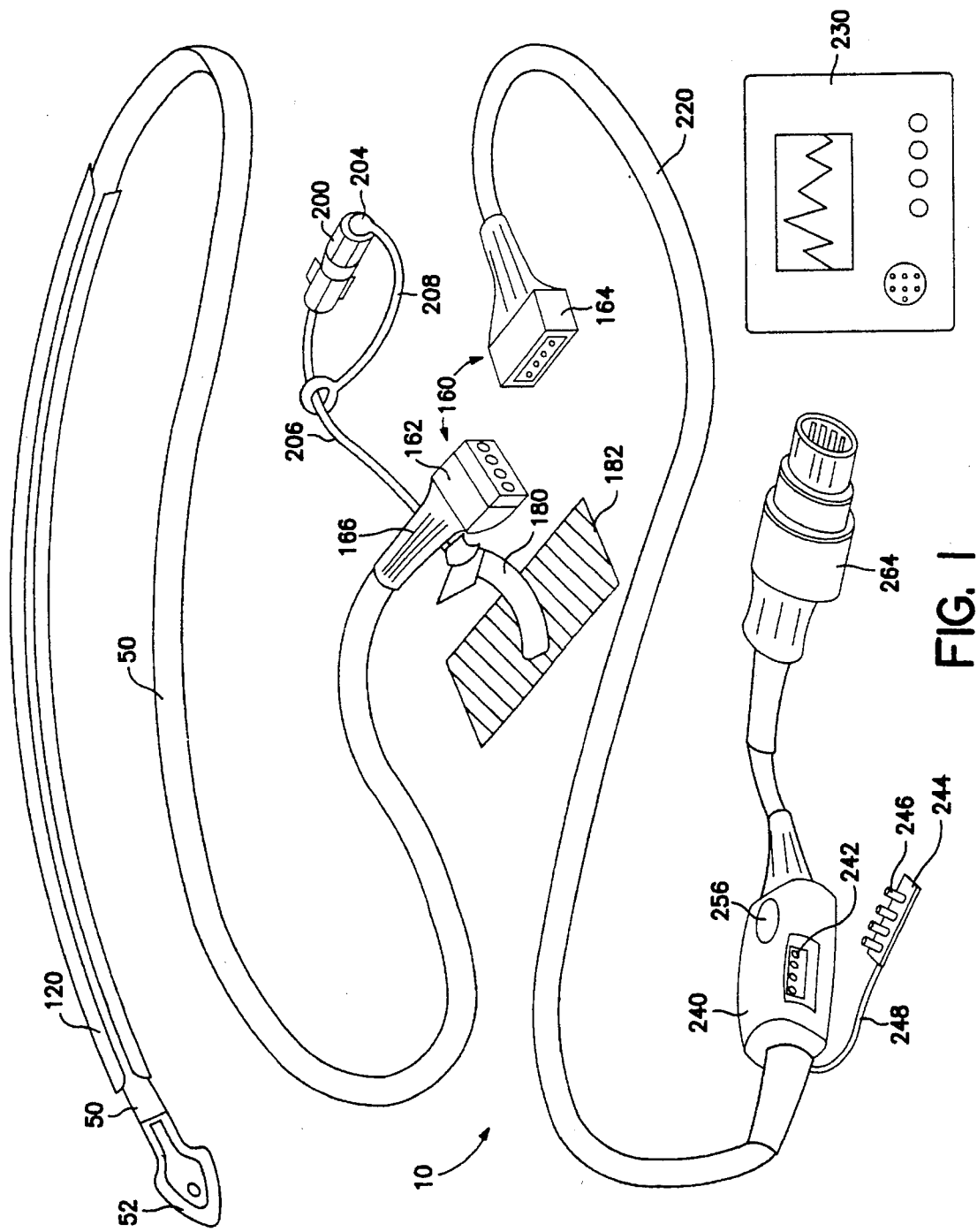
FIG. 1 is a perspective view of one embodiment of the transducer-tipped intrauterine pressure catheter system illustrating the components of that system according to the present invention.

Referring now to the drawing, wherein like reference numerals refer to like elements throughout, FIG. 1 is a perspective view of a first embodiment of the transducer-tipped intrauterine pressure catheter system 10 illustrating the components of that system according to the present invention. It is emphasized that, according to common practice, the various elements of the drawing are not to scale. On the contrary, the width or length and thickness of the various components are arbitrarily expanded or reduced for clarity.

Intrauterine pressure catheter system 10 has a pressure sensor 20 embedded in a tip 52 of catheter 50. An introducer 120 allows the user to manipulate catheter 50 to position tip 52 and, therefore, sensor 20 properly within the uterus. A connector assembly 160, having a female connector socket 162 and a male connector plug 164 as its two, main components, electrically connects sensor 20 with monitor cable 220. In turn, monitor cable 220 electrically connects sensor 20 to external monitor 230 via monitor pin connector 264. A test member 240 is provided to assure that male connector plug 164, monitor cable 220, and monitor pin connector 264 are operational. Push button 256 can be depressed to zero system 10 at any time during use. Connector assembly 160 is secured to the thigh or abdomen of the mother using an adhesive attachment pad 182 and an attachment strap 180. To permit infusion of fluid into the amniotic sac, a luer fitting 200 is connected to catheter 50 in the body 166 enclosing female connector socket 162.

I. Sensor

Figure 2:
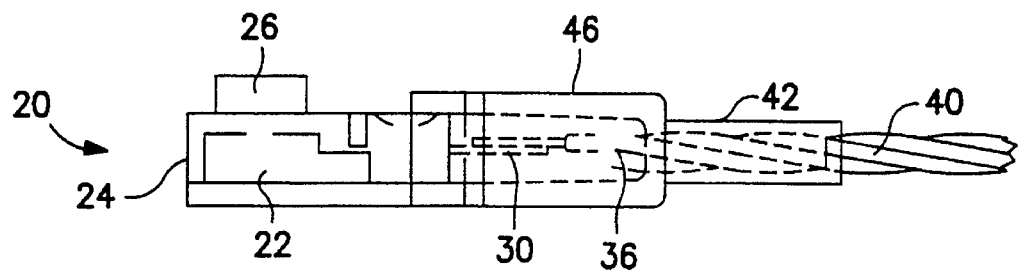
FIG. 2 is a side view, in partial cross section, of the conventional pressure sensor incorporated in the present invention.
Figure 3:
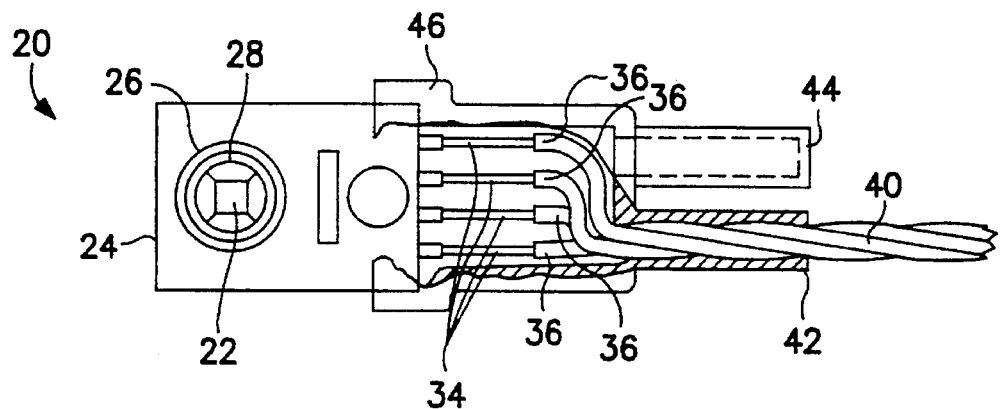
FIG. 3 is a top view of the pressure sensor illustrated in FIG. 2.
Figure 4:
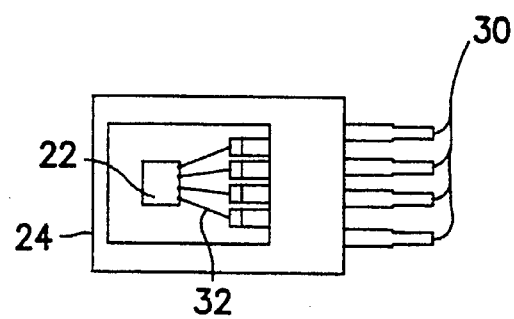
FIG. 4 is a cut-away, top view of the pressure sensor illustrated in FIG. 3 highlighting its circuitry.

Sensor 20 incorporated in intrauterine pressure catheter system 10 of the present invention will now be discussed in detail with reference to FIGS. 2, 3, and 4. Sensor 20 is a conventional, miniature silicon diaphragm pressure sensor that can directly read pressures during labor when introduced into the amniotic sac transcervically. Obstetric caregivers can use this pressure data to properly assess the progression of labor. Sensor 20 must be a sufficiently low-cost, high-volume element to be disposable.

Like most conventional, miniature pressure sensors, sensor 20 has a thin diaphragm (not shown) which can be deflected by the pressure pulses traveling through the uterine fluid. Some type of mechanism is also provided to measure the deflection of the diaphragm, including electronic circuitry configured to generate an electrical signal representing the pressure exerted on the diaphragm. Although a variety of electronic mechanisms have been used to measure diaphragm deflection, a resistive strain gauge is suitable. A more recent technology involves integrated circuitry. By special processing, the diaphragm can be made from silicon with resistive material (such as Boron) diffused into the silicon in the form of a Wheatstone bridge. Using this type of diaphragm-circuitry configuration, very precise measurements of even small pressure pulses acting on the pressure diaphragm can be obtained.

A suitable sensor 20 is commercially available from Motorola, Inc. as Model MPX2300D. A piezoresistive strain gauge implant, thin-film temperature compensation element, and calibration element are all integrated on a single, monolithic, semiconductor die 22. Die 22 is encased in polysulfone housing 24. Motorola Chip Pak Element Case 423 is suitable. The pressure range which sensor 20 can monitor is −30 to 300 mmHg.

Sensor 20 has an orifice 26 protruding from the top of housing 24 above die 22. A silicon dielectric gel 28 fills orifice 26 and protects the electrical components of sensor 20 from the wet environment in which system 10 operates. (A "gel" is a jellylike substance formed by the coagulation of colloidal solution into a solid phase.) This increases the safety of system 10 by helping to minimize any electrical shock hazard to the patient. Gel 20 permits pressure gradients, however, to reach the diaphragm of sensor 20.

Die 22 is electrically connected to a number (four are shown) of electrical connector pins 30 via leads 32. Connector pins 30 may be gold-plated phosphor bronze. In turn, connector pins 30 are electrically connected via solder 34 to a corresponding number of wires 36 which comprise leadwire cable 40. All of the elements of sensor 20 are mounted on an armature 46. Leadwire cable 40 travels away from sensor 20 through the port 42 of armature 46. Armature 46 also has a solid plug 44 which lies parallel to port II. Tip Design The prior art discloses several mechanisms by which sensor 20 (including its pressure transducer) is mounted to tip 52 of catheter 50. U.S. Pat. No. 4,712,566 issued to Hök, for example, discloses a transducer mounted on a movable guide sliding within the catheter. U.S. Pat. No. 5,050,297 issued to Metzger discloses a transducer mounted on a rigid support member sized and shaped to fit into a lumen of the catheter. U.S. Pat. No. 4,274,423 issued to Mizuno et al. discloses a transducer mounted non-rigidly to the support member of the catheter (a soft, silicon rubber is disposed around the sensor).

Figure 5:
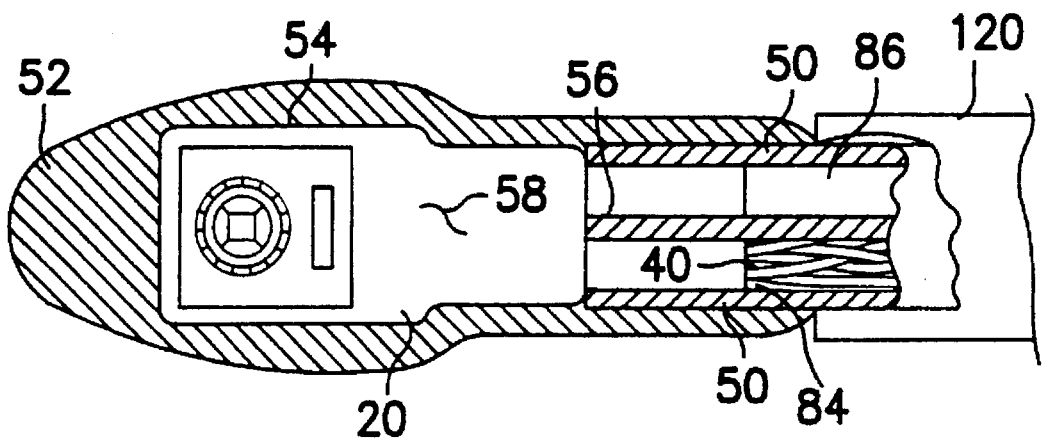
FIG. 5 is a top view illustrating the pressure sensor in position in one embodiment of the catheter tip according to the present invention.
Figure 6:
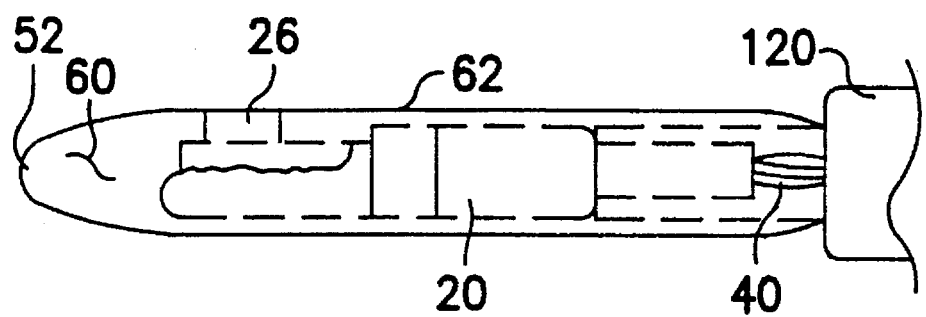
FIG. 6 is a side view of the catheter tip and pressure sensor combination illustrated in FIG. 5.

Turning to FIGS. 5 and 6, sensor 20 is mounted in a fixed, rigid manner within the tip 52 of catheter 50 and not in a lumen of catheter 50. Thus, the size and shape of catheter 50 (in which the lumens travel) need not be adapted to accommodate sensor 20. In addition, system 10 does not require "leveling" sensor 20 at a particular anatomical reference point when zeroing system 10 because the pressure is measured at tip 52 of catheter 50.

As stated above, all of the components of sensor 20 are mounted on armature 46. A sealant 54 is applied to seal sensor 20 on armature 46. Sealant 54 may be prepared by dissolving polycarbonate resin in a methylene chloride solvent. Other methods to bond the components could be used. Next, armature 46 is bonded to catheter 50 using an adhesive 56. Preferably, adhesive 56 is urethane. Then a silicone primer 58 is applied to all external surfaces of sensor 20 and armature 46 and to certain surfaces of catheter 50. A flexible elastomer 60 (silicon rubber or thermoplastic rubber) is molded around the assembled components to form a soft, broad, and flat tip 52 that reduces the possibility of fetal or uterine trauma as catheter 50 is inserted. In this way, sensor 20 is rigidly fixed in tip 52 of catheter 50.

Orifice 26 of sensor 20 must not protrude above the top surface 62 of tip 52; otherwise, the risk of not obtaining a good trace arises. Orifice 26 fills with fluid during use and it is believed that a meniscus forms, if orifice 26 protrudes above top surface 62, which affects the pressure reading of sensor 20. There is also a safety problem if orifice 26 protrudes above top surface 62. Accordingly, it is preferable to recess orifice 26 slightly within top surface 62 of tip 52.

Silicon gel 28 must not exit orifice 26 of sensor 20 during use. Accordingly, a membrane (not shown) may be placed over orifice 26 to retain silicon gel 28. Alternatively, a cap (not shown) may be placed over orifice 26 to narrow the opening of orifice 26 at top surface 62.

With respect to the design of tip 52 of catheter 50, the size of sensor 20 defines the size of tip 52. A smaller sensor 20 permits a smaller tip 52. Thus, sensor 20 should be selected to be as small as feasible to accommodate a 2 cm cervical dilation. Otherwise, conventional catheter tip designs fail to suggest that any particular size or shape is more or less desirable.

Figure 7:
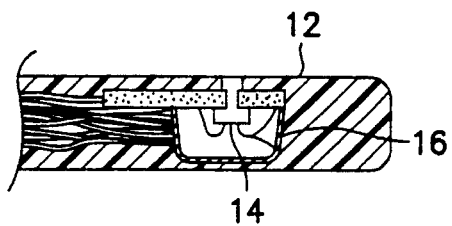
FIG. 7 is a cross-sectional view of a conventional tip design for an intrauterine pressure catheter.
Figure 8:
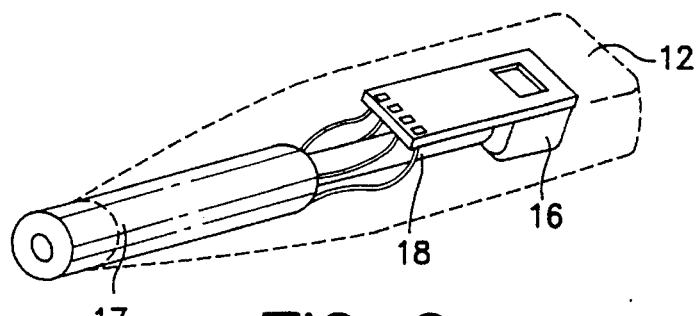
FIG. 8 is a perspective view of the conventional tip design illustrated in FIG. 7 with the flexible boot forming the tip shown by broken lines.

U.S. Pat. No. 4,873,986 issued to Wallace discloses a disposable transducer-tipped intrauterine pressure catheter. The tip design of the '986 patent is a symmetrical, blunt, flexible boot 12 covering a semiconductor pressure transducer 14 which is mounted in a cap 16. See FIGS. 7 and 8 (which correspond to FIGS. 2 and 3 of the '986 patent, respectively). Boot 12 is about 0.35 inches (0.77 cm) by 0.2 inches (0.44 cm) by 0.61 inches (1.34 cm). See '986 patent at column 10, lines 31–33.

To facilitate insertion of boot 12 into the uterus, cable 17 is provided with a stiffener: stranded steel stylet 18. At column 8, lines 1–4, the '986 patent states: "Boot 12 may have virtually any suitable configuration which will allow for insertion of boot 12 into the uterus or other body compartment for which the apparatus is designed." The '986 reference teaches, therefore, that the configuration of the tip for a transducer-tipped intrauterine pressure catheter is not critical.

Figure 9:
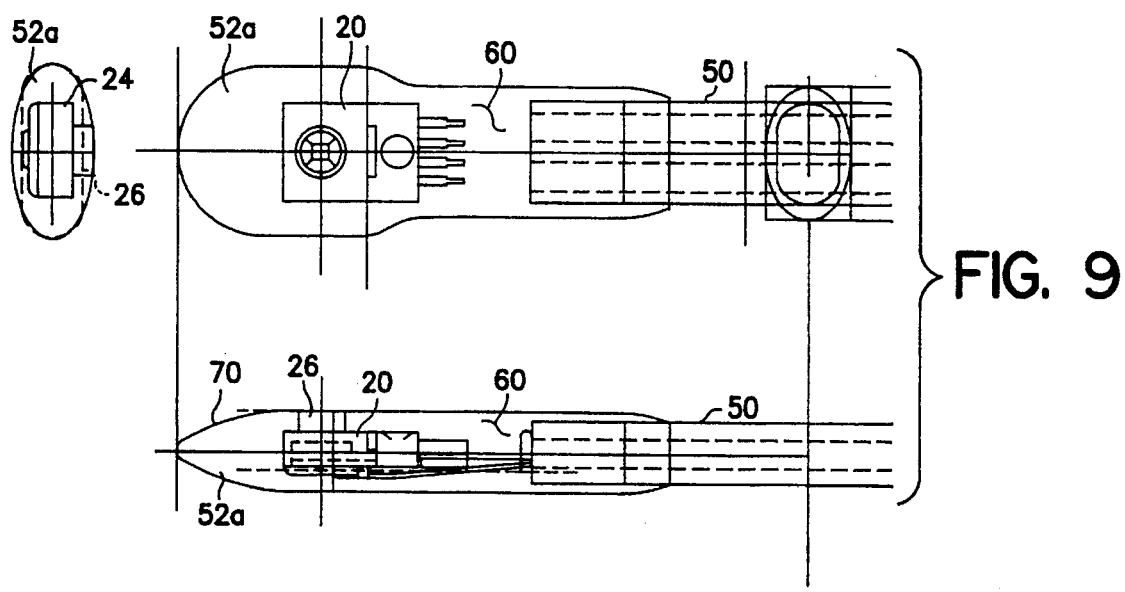
FIG. 9 provides a top view, opposing end views, and a side view of a relatively rounded catheter tip design in accordance with the present invention.
Figure 10:
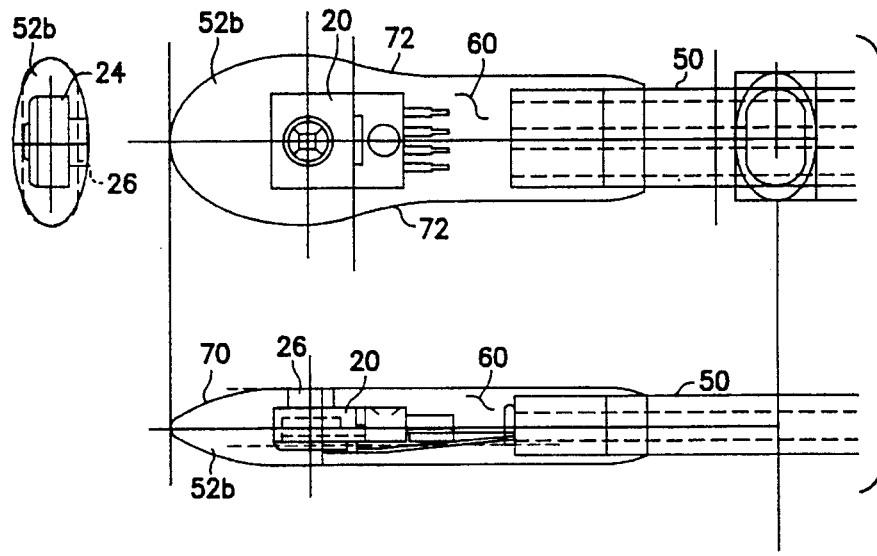
FIG. 10 provides a top view, opposing end views, and a side view of an intermediate catheter tip design in accordance with the present invention.
Figure 11:
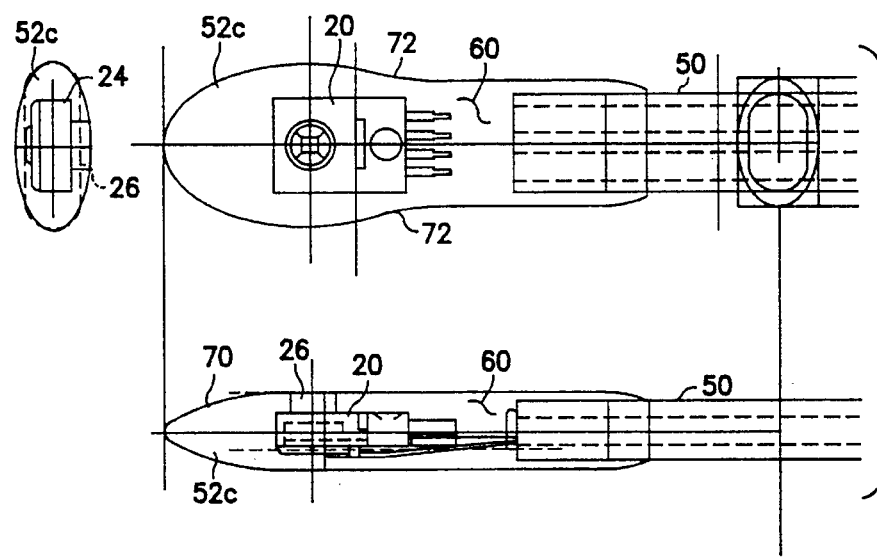
FIG. 11 provides a top view, opposing end views, and a side view of a relatively pointed catheter tip design in accordance with the present invention.

This is not true. To further improve the reliability of the pressure data provided by sensor 20, the physical design of tip 52 of catheter 50 provides a unique profile which uses fetal placement and the anatomy of the birth canal to better control catheter movement and orientation during and after insertion. Three exemplary designs for tip 52 are illustrated in FIGS. 9, 10, and 11. Each illustration provides a top view, opposing end views, and a side view of the tip. FIG. 9 shows a tip 52a which is the most rounded; FIG. 11 shows a tip 52c which has the most narrow apex; and FIG. 10 shows an intermediate tip 52b which is more pointed than rounded tip 52a and more rounded than tip 52c.

The alternative tips 52a, 52b, and 52c each have a taper 70 to separate tissue and ease insertion of catheter 50; taper 70 reduces the force required for placement. Because each tip 52a, 52b, and 52c is made of soft elastomer 60, insertion of catheter 50 is relatively comfortable for the patient. Each design is broad and flat, having a width greater than its height, to further facilitate insertion and orientation of the tip. There are no corners or notches to impede placement. The soft, broad, and flat catheter tips 52a, 52b, and 52c greatly reduce the possibility of fetal or uterine trauma during the insertion and placement procedure and help insure reliable positioning between maternal and fetal tissues.

Catheter tips 52a, 52b, and 52c each have a maximum height of about 0.2 inches (0.5 cm) and taper to the apex of the tip (at which the height is zero) over a distance of about 0.4 inches (1.0 cm). Each tip is about 0.43 inches (1.1 cm) at its widest point and tapers to the apex of the tip (at which the width is zero) over a distance of between 0.4 and 0.47 inches (1.0 and 1.2 cm). Each tip is about 1.3 inches (3.3 cm) long.

The asymmetric shape of each tip 52a, 52b, and 52c informs the user which side of sensor 20 faces which way so that orifice 26 can be positioned properly. Each tip also has an undercut 72 to reduce catheter slippage once catheter 50 is positioned inside the uterus. Thus, the catheter tip profile is designed for patient comfort, easy insertion, and assured positioning resistant to slippage. In contrast, the blunt tip geometry of the conventional tip designs makes insertion relatively difficult. Moreover, those designs do not have an undercut to resist slippage. The main reason for failure of conventional intrauterine pressure catheter systems is that the catheter slips or relocates due to movement.

It is imperative that sensor 20 in tip 52 contact the desired tissue once catheter 50 is inserted. Accordingly, the orientation of sensor 20 and, therefore, of tip 52 during use is important. Because conventional tip designs may be symmetrical, they may position the orifice of the pressure transducer improperly in the uterus. Tips 52a, 52b, and 52c are each asymmetrical, assuring correct positioning of orifice 26. The asymmetric shape of tips 52a, 52b, and 52c assures that the tip "self-corrects" as it is inserted through tissue so that the tip is positioned in one of two positions: up or down. In either case, sensor 20 will contact tissue. Moreover, the asymmetric shape informs the user which side of sensor 20 faces which way. In contrast, the symmetric geometry of the conventional designs has no "directionality" and neither assures placement of the transducer in contact with tissue nor provides the user with information (the transducer could be located anywhere around the 360° circumference of the tip).

The ability of tip 52 to prevent catheter 50 from slipping once positioned in the uterus is important. Because the uterus retains a certain amount of amniotic fluid after the membranes rupture, the actual pressure at any point within the uterus will vary depending on the relative height of the amniotic fluid directly above that point. The fluid weight exerts a hydrostatic pressure of approximately 2 mmHg per inch of fluid height.

Depending on the diameter of the uterus, the amount of amniotic fluid retained, and the position of the mother, the effective hydrostatic fluid pressure can theoretically add as much as 20 to 25 mmHg to all pressure readings. Typically, however, the effects are much lower and are in the range of 5 to 10 mmHg. Because the baseline pressure and the peak pressures are effected equally, there is no net effect on the amplitude (height) of the displayed contraction.

Sensor 20 will sense the actual pressure within the uterus at the exact position where tip 52 of catheter 50 rests. If tip 52 were to move, the pressure reading might change. For example, if the new position of tip 52 is higher than the previous position, the hydrostatic fluid pressure will be less and the pressure reading will be lower.

U.S. Pat. No. 4,543,965 issued to Pack et al. recognizes the need to fix an intrauterine pressure catheter in position. The '965 patent discloses an elongated, flexible catheter having a broad uterine end. An inflatable membrane anchors the catheter in the uterus. The '965 patent fails to disclose or suggest, however, a specific catheter geometry to achieve the function of anchoring the catheter. Soft, broad, and flat catheter tips 52a, 52b, and 52c—each having an undercut 72—function to position catheter 50 in the uterus. Thus, these features, and not an inflatable membrane, are used to accomplish the anchoring function for catheter system 10.

III. Catheter

Like sensor 20, catheter 50 is a sterile, disposable (meaning single patient use) component. Thus, catheter 50, tip 52, and sensor 20 are all discarded after use. Catheter 50 is firm, flexible, flat, and does not require fluid filling. Preferably, catheter 50 is an extruded thermoplastic elastomer such as polyurethane. Suitable dimensions for catheter 50 are a length of about 30 inches (75 cm), a width of about 0.265 inches (0.67 cm), and a height of about 0.150 inches (0.38 cm).

The more flexible is catheter 50, the more comfortable the patient finds its use. But an overly flexible catheter 50 is difficult to maneuver and control. Accordingly, a tradeoff exists: stiffer catheters allow for ease of insertion while flexible catheters enhance patient comfort. (An overly rigid or stiff catheter 50 is also difficult to maneuver and may cause placental injury.) Depending upon which design characteristic is determined to be more important—comfort or ease of insertion, the stiffness of catheter 50 can be adjusted accordingly. Typically, catheter 50 has a hardness, as measured by a durometer, in the range between 80 Shore A and 98 Shore A and, more particularly, between 85 and 92 Shore A (92 Shore A corresponds to a 45D hardness). Introducer 120 is unnecessary when using catheter 50 of such hardness; catheter 50 is sufficiently stiff to permit handling and ease insertion—yet catheter 50 is sufficiently flexible to assure patient comfort. Relatively rigid introducer 120 may be used anyway, to facilitate insertion, or in conjunction with catheter 50 having more flexibility and reduced stiffness.

As discussed above, U.S. Pat. No. 4,873,986 discloses a disposable transducer-tipped intrauterine pressure catheter. See FIGS. 7 and 8 (which correspond to FIGS. 2 and 3 of the '986 patent, respectively). To facilitate insertion of boot 12 into the uterus, cable 17 is provided with a stiffener: stranded steel styler 18. Thus, the '986 patent discloses a stranded steel stylet, internal to the catheter, to facilitate insertion of the catheter. One of the advantages of catheter 50 according to the present invention is that catheter 50 does not require a stiffener.

FIGS. 12a, 12b, 12c, and 13 illustrate a first embodiment of catheter 50 disposed along longitudinal axis "b". Catheter 50 is connected on its first end 80 to catheter tip 52 as discussed above. Specifically, catheter 50 is joined to catheter tip 52 (in which sensor 20 is rigidly fixed) by molding elastomer 60 around the assembled components. The second end 82 of catheter 50 is joined to connector assembly 160 in a manner described below.

Catheter 50 has at least two lumens. The first embodiment of catheter 50 shown in FIGS. 12a, 12b, 12c, and 13 has precisely two lumens: cable lumen 84 and amnio lumen 86. Amnio lumen 86 has an internal diameter of about 0.08 inches (0.20 cm) and an outer diameter of about 0.125 inches (0.32 cm). Leadwire cable 40 from sensor 20 travels through cable lumen 84 and ends in female connector socket 162 of connector assembly 160. A vent hole 88, drilled in catheter 50, emanates from cable lumen 84 and is located near connector assembly 160.

Sensor 20 vents to the atmosphere through cable lumen 84, traversing catheter 50, and vent hole 88. For the pressure transducer of sensor 20 to function properly, the diaphragm must be vented on one side to a substantially constant pressure. Typically, one side of the diaphragm of the transducer is continuously vented to atmospheric pressure. Vent hole 88 may have a diameter of about 0.045 inches (0.11 cm), be centered in the side of catheter 50, and be positioned 1.25 inches (3.2 cm) from second end 82 of catheter 50.

Thus, cable lumen 84 simultaneously carries leadwire cable 40 and provides a vent for sensor 20 through catheter 50. Leadwire cable 40 typically is a bundle of four wires 36 connected on one end to connector pins 30 of sensor 20 and on the opposite end to female connector socket 162 of connector assembly 160. Each wire 36 has Teflon™ insulation.

Amnio lumen 86 traverses catheter 50 between sensor 20 and luer fitting 200. Amnio lumen 86 may function to permit amnio-infusion, amniotic fluid sampling, or a pressure conduit to zero sensor 20 to an atmospheric reference pressure. A first amnio port 90 and a second amnio port 92, each drilled in catheter 50, emanate from amnio lumen 86 and are located near catheter tip 52. First amnio port 90 exits catheter 50 at its top face, may have a diameter of about 0.045 inches (0.11 cm), may be centered about 0.075 inches (0.20 cm) from the side of catheter 50, and may be positioned about 2.25 inches (5.7 cm) from first end 80 of catheter 50. Second amnio port 92 exits catheter 50 at its side face, may have a diameter of about 0.045 inches (0.11 cm), may be centered in the side of catheter 50, and may be about 1.25 inches (3.2 cm) from first end 80 of catheter 50. Thus, amnio ports 90 and 92 are on different sides of catheter 50 and are separated by about one inch; therefore, if one amnio port becomes blocked (by clotted blood or other biological debris present within the uterus) the other is likely to remain functional.

As described above, armature 46 of sensor 20 has solid plug 44 and port 42. Port 42 fits tightly within cable lumen 84. Thus, leadwire cable 40 travels away from sensor 20 through port 42 of armature 46 of sensor 20 and into cable lumen 84. Port 42 and cable lumen 84 also combine to vent sensor 20. Solid plug 44 of armature 46 of sensor 20 fits tightly within amnio lumen 86. Thus, solid plug 44 stops amnio lumen 86.

In addition to cable lumen 84 and amnio lumen 86, catheter 50 may have one or more additional lumens to provide (like amnio lumen 86) amnio-infusion, amniotic fluid sampling, or a pressure conduit to zero sensor 20 to an atmospheric reference pressure. FIG. 15 illustrates a second embodiment of catheter 50 having a third lumen 94. Multiple lumens 84 and 86, and possibly 94, allow system 10 to monitor intrauterine pressure and deliver infusible fluids simultaneously.

Catheter 50 has, on its top surface, a first position indicator 96 located 12 inches (30 cm) from first end 80 of catheter 50 and a second position indicator 98 located 18 inches (45 cm) from first end 80 of catheter 50. First position indicator 96 may be a dark, solid line. Second position indicator 98 may consist of two, dark, solid lines to distinguish second position indicator 98 from first position indicator 96. First indicia 100, such as "30 cm", may be positioned adjacent first position indicator 96. Similarly, second indicia 102, such as "45 cm", may be positioned adjacent second position indicator 98. Position indicators 96 and 98 inform the user how far catheter 50 has been inserted.

FIGS. 14a, 14b, and 15 illustrate a second embodiment of catheter 50. A handle 104 is provided on catheter 50 in the area around first position indicator 96. Handle 104 facilitates movement of catheter 50 by the user and eases the procedure by which catheter 50 is inserted and positioned. The flared region 106 of handle 104 will be positioned in the introitus area when catheter 50 is fully inserted. Flared region 106 helps to reduce the risk that catheter 50 will slip out of position once fully inserted.

U.S. Pat. No. 4,722,730 issued to Levy et al. discloses a device that includes two intrauterine pressure catheters each having its own lumen. The catheters (and lumens) are bonded in a substantially contiguous spaced relationship, with a weakening point along the bonding permitting the catheters (and lumens) to be separated at the weakening point and, thereby, to assume a non-contiguous relationship. A guide tube is required to provide passage of the catheter assembly into the uterus.

Figure 16:
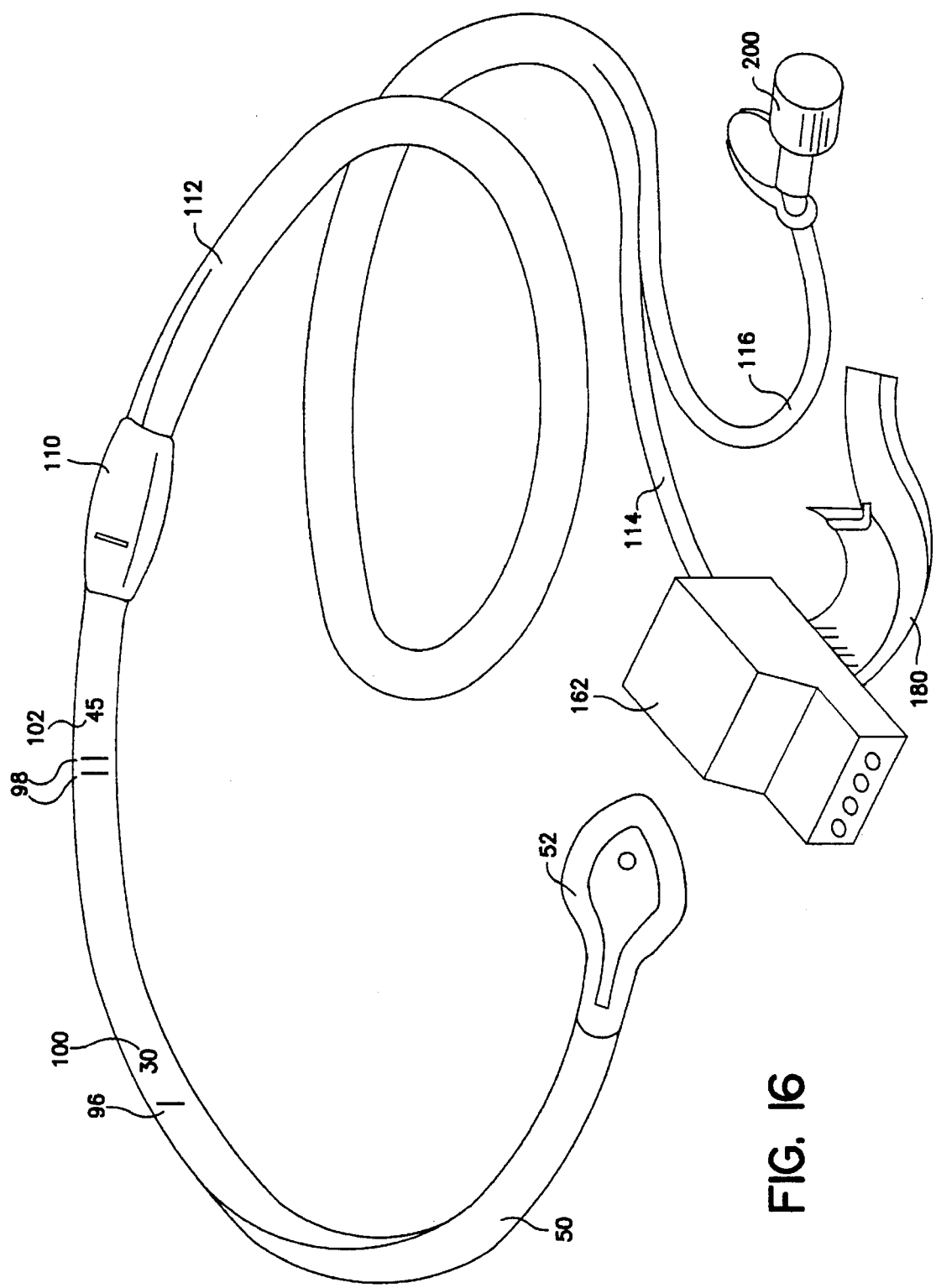
FIG. 16 is a perspective view of a third embodiment of the catheter in accordance with the present invention.

The third embodiment of catheter 50 illustrated in FIG. 16 improves upon the concept of separate catheters disclosed in the '730 patent. In the first two embodiments of catheter 50 discussed above, catheter 50 ends, at second end 82, in connector assembly 160. Second end 82 of catheter 50 ends, in the third embodiment shown in FIG. 16, in a junction 110. A conventional, peelable, amnio-cable paratubing 112 is connection to junction 110 opposite catheter 50. Paratubing 112 has a first line 114 and a second line 116, each having its own, separate lumen (neither lumen is shown). First and second lines 114 and 116 (with their respective lumens) are bonded in a substantially contiguous spaced relationship, with a weakening point along the bonding permitting lines 114 and 116 (and their respective lumens) to be separated at the weakening point and, thereby, to assume a non-contiguous relationship.

First line 114 and its lumen carry leadwire cable 40 from catheter 50 to connector assembly 160. Similarly, second line 116 and its lumen continue amnio lumen 86 from catheter 50 to luer fitting 200. In order to achieve the advantages of catheter 50 and to combine catheter 50 with paratubing 112, junction 110 must be provided between catheter 50 and paratubing 112. The first and second embodiments of catheter 50 discussed above eliminate paratubing 112 and, therefore, avoid the necessity of junction 110 between paratubing 112 and catheter 50.

IV. Slotted Introducer

As discussed above, introducer 120 is optional when using catheter 50 of sufficient stiffness to permit handling and to ease insertion of catheter 50. Relatively rigid introducer 120 may be used anyway, to facilitate insertion, or in conjunction with catheter 50 having more flexibility and reduced stiffness. Introducer 120 avoids the need to provide catheter 50 with a stiffener even when a relatively rigid catheter 50 is desired.

Guide tubes are well known devices to help insert medical devices into body cavities. U.S. Pat. No. 3,827,428 issued to Hon et al., for example, discloses a circular, completely enclosed guide tube used to insert a bipolar electrode structure for monitoring fetal heartbeat. The '730 patent (discussed above) discloses an elliptical, completely enclosed guide tube used to insert an apparatus for simultaneously monitoring intrauterine pressure and delivering infusible fluids. As discussed below, introducer 120 represents an improvement over conventional guide tubes.

FIGS. 17, 18, 19, and 20 illustrate introducer 120 according to the present invention. Introducer 120 engages catheter 50 to permit handling and to ease insertion of catheter 50. Because introducer 120 has a longitudinal slot disposed along its entire length, introducer 120 can be removed and discarded once catheter 50 is inserted. Introducer 120 is extruded and formed from a polyolefin (preferably from high-density polyethylene). As shown disposed along longitudinal axis "c" in FIG. 17, introducer 120 has a length of about 10 inches (25.4 cm). Introducer 120 may be shaped, as shown in FIG. 18, with a gentle curve to conform comfortably with the shape of the vagina and cervix of a woman in labor.

Introducer 120 has a longitudinal slot 122, an open front end 124, and an open back end 126. Slot 122 is placed in the bottom of introducer 120. Such a design is consistent with U.S. Pat. No. 4,644,757 issued to Ricciardelli et al. Distinguish slotted introducer 120 from a guide tube having a slit. Longitudinal slot 122 is sufficiently wide to permit easy removal of catheter 50 from introducer 120 once catheter tip 52 has been placed. A "slit" guide tube, such as that of the INTRAN PLUS™ design available from Utah Medical Products, Inc., does not have any space in the resting position; the slit guide tube forms a completed, closed tube in the resting position. In contrast, slotted introducer 120 has a space—slot 122—forming a "C"-shape, in the resting position.

Slotted introducer 120 offers a number of functional advantages over the slit guide tube. It is difficult, relative to the slotted introducer 120, both to remove catheter 50 from, and to insert catheter 50 into (upon assembly), the slit guide tube. Thus, a tab is required on the slit guide tube to allow the user to exert sufficient force on the slit guide tube to peel it away from catheter 50. No such tab is required to remove slotted introducer 120. In addition, slot 122 in introducer 120 allows introducer 120 to bend while the exit position of slot 122 is controlled. In contrast, when the slit guide tube is bent, the opening of the slit "travels."

FIG. 19 is an enlarged view of front end 124 of introducer 120. The top 128 of both the first side wall 130 and the second side wall 132 of introducer 120 has a radius or chamfer 134 on front end 124. The bottom 136 of both first side wall 130 and second side wall 132 of introducer 120 has a radius 138 on front end 124. FIG. 20 is a side view taken along the line 20—20 of FIG. 18. As shown in FIG. 20, bottom 136 of both first side wall 130 and second side wall 132 of introducer 120 has a blended radius 140 on front end 124.

Chamfer 134, radius 138, and blended radius 140 on front end 124 of introducer 120 prevent any sharp edges on front end 124 of introducer 120. Accordingly, these design features increase safety in using intrauterine catheter system 10. Chamfer 134, radius 138, and blended radius 140 may be formed by flame treating front end 124. Alternatively, front end 124 of introducer 120 may be insert molded as an integral component of the extruded introducer 120.

Figure 21A:
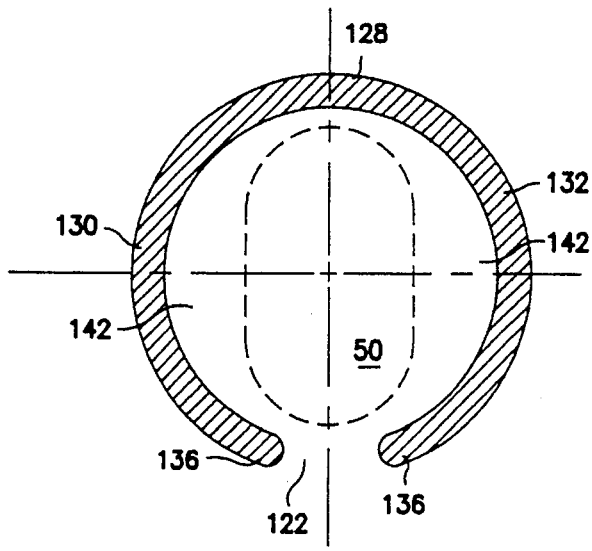
FIGS. 21a, 21b, 21c, and 21d illustrate four possible cross sections for the introducer in accordance with the present invention.

Introducer tube 120 has a C-shaped cross section. FIGS. 21a, 21b, 21c, and 21d illustrate four possible cross-sections for introducer 120. FIG. 21a shows a round or circular cross section, like that disclosed in the '757 patent, having a diameter of about 0.30 inches (0.76 cm). The thickness of side walls 130 and 132, top 128, and bottom 136 is substantially uniform (typically about 0.030 inches (0.076 cm)). Slot 122 is about 0.085 inches (0.22 cm) wide.

Figure 21B:
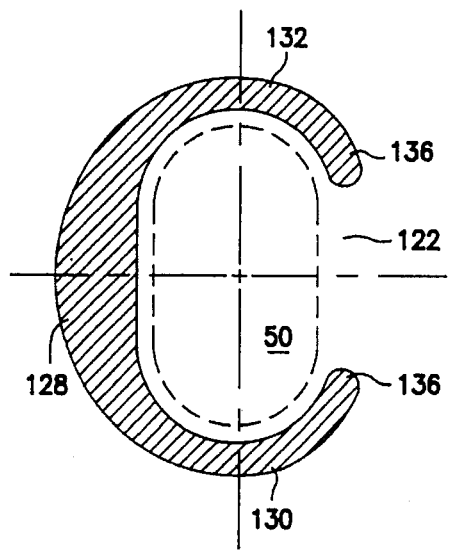
Figure 21D:
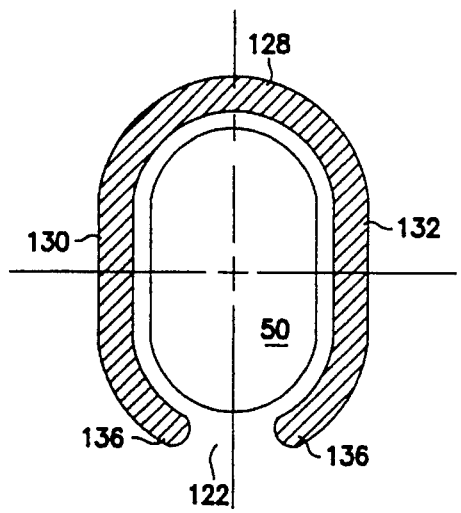
Figure 21C:
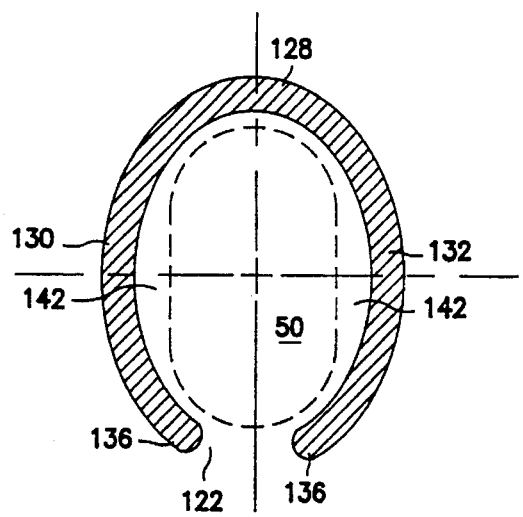
Figure 22F:
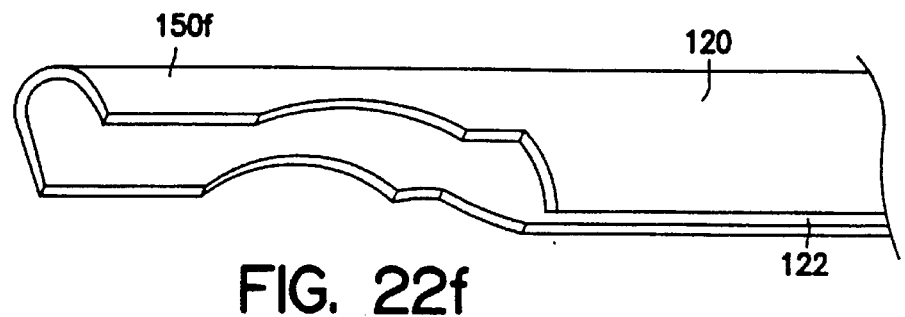
Figure 22G:
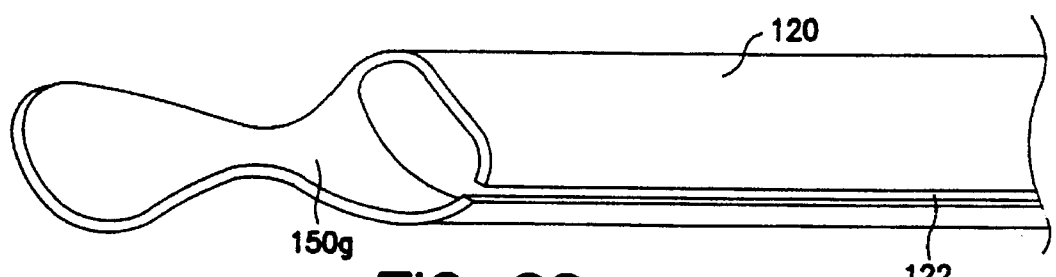

FIG. 21c shows an oval or elliptical cross section. The minor axis of the elliptical cross section is about 0.200 inches (0.5 cm) and the major axis is about 0.300 inches (0.76 cm). The thickness of side walls 130 and 132, top 128, and bottom 136 is substantially uniform (typically about 0.030 inches (0.076 cm)). Slot 122 is about 0.085 inches (0.22 cm) wide.

For both of the alternative cross sections shown in FIGS. 21a and 21c, gaps 142 exist between catheter 50 and side walls 130, 132. Consequently, catheter 50 can turn within introducer 120. Such movement reduces the effectiveness of introducer 120 when used to position catheter tip 52. In addition, the presenting part of catheter 50 to slot 122 is a narrower side of catheter 50 rather than the wider top surface of catheter 50. Accordingly, the width of slot 122 is restricted somewhat (it must not be larger than the width of the presenting side of catheter 50) to assure that catheter 50 does not inadvertently exit introducer 120. This makes removal of catheter 50 from introducer 120 more difficult. Finally, the restricted width of slot 122 and the uniform thickness of walls 130, 132 of introducer 120 may tend to collapse (i.e., "wrinkle") walls 130, 132 upon significant bending.

FIG. 21d shows an oval or elliptical cross section which parallels the geometry of catheter 50. Consequently, catheter 50 cannot turn within introducer 120 and introducer 120 can be used most effectively to position catheter tip 52. The minor axis of the elliptical cross section is about 0.180 inches (0.46 cm)—about 0.030 inches (0.076 cm) greater than the height of catheter 50—and the major axis is about 0.300 inches (0.76 cm)—about 0.030 inches (0.076 cm) greater than the width of catheter 50. The thickness of side walls 130 and 132, top 128, and bottom 136 is substantially uniform (typically about 0.030 inches (0.076 cm)). Slot 122 is about 0.085 inches (0.22 cm) wide. As for the alternative cross sections illustrated in FIGS. 21a and 21c, removal of catheter 50 having the cross section of FIG. 21d from introducer 120 is relatively difficult and walls 130, 132 of introducer 120 may tend to collapse upon significant bending.

The cross section for introducer 120 illustrated in FIG. 21b is preferred. The geometry of the preferred cross section of introducer 120 is flat, not round. As illustrated, introducer 120 has an oval or elliptical cross-section which parallels the geometry of catheter 50. Consequently, catheter 50 cannot turn within introducer 120 and introducer 120 can be used most effectively to position catheter tip 52. The minor axis of the elliptical cross section is about 0.180 inches (0.46 cm) and the major axis is about 0.300 inches (0.76 cm), as for the cross section illustrated in FIG. 21d, but the axes have been reversed. Thus, the presenting part of catheter 50 to slot 122 is the wider top surface rather than the narrower side of catheter 50. Accordingly, the width of slot 122 (approximately 0.165 inches (0.42 cm)) is about twice that of the alternative cross sections without risk that catheter 50 will inadvertently exit introducer 120. This facilitates removal of catheter 50 from introducer 120. In summary, the asymmetric shape of introducer 120 allows it to peel away from catheter 50 most easily and prevents it from catching on catheter 50.

The cross section for introducer 120 illustrated in FIG. 21b has a top with a thickness of about 0.030 inches (0.076 cm)—the same as for the alternative cross sections. The thickness (about 0.080 inches (0.20 cm)) of top 128 opposite slot 122 is much greater, however, than that for the alternative cross sections. Side walls 130 and 132 form a transition from the bottom thickness of about 0.030 inches (0.076 cm) to the top thickness of about 0.080 inches (0.20 cm). The non-uniform wall thickness provides a number of functional advantages, including improved shape retention (or "memory"), reduced tendency of walls 130, 132 to collapse upon significant bending, and easier removal of introducer 120 without pulling or catching on catheter 50.

Although introducer 120 can be removed from catheter 50 with relative ease following placement of catheter 50, a grip 150 may be provide on introducer 120 to further ease removal. FIGS. 22a, 22b, 22c, 22d, 22e, 22f, and 22g illustrate alternative embodiments for grip 150 on introducer 120. Grip 150a is a strap having an opening which the user can grasp to pull introducer 120 away from catheter 50 in a direction opposite slot 122 of introducer 120. Grip 150b is a similarly oriented but solid strap. Grip 150c is formed by removing a section of introducer 120. Grip 150d is a strap which is looped about catheter 50. A slit in the strap separates when the user pulls on grip 150d. One advantage of handles 150c and 150d over handles 150a and 150b is that dangling portions of the grip, which might catch and inadvertently separate introducer 120 from catheter 50, are avoided.

Figure 23:
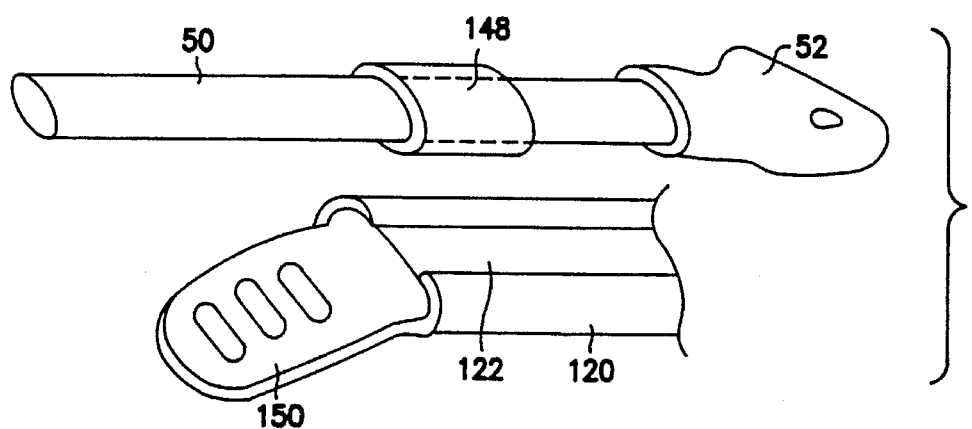
FIG. 23 illustrates an exemplary grip on the introducer in combination with an insert-molded collar on the catheter in accordance with the present invention.

Grip 150e has a pair of tabs. The user removes introducer 120 by compressing the tabs of grip 150e in the direction of the arrows shown in FIG. 22e and pulling downward away from slot 122. Grip 150f has finger recesses which enable the user to better grasp the grip. Grip 150g similarly has finger recesses. FIG. 23 illustrates grip 150 on introducer 120. Also shown is an insert-molded collar 148 on catheter 50. Collar 148 can simplify the construction of catheter 50 and help to retain catheter 50 in its fully inserted position. Introducer 120 engages collar 148. Although one collar 148 is shown in FIG. 23, multiple collars may be provided on catheter 50.

V. Anti-Bacterial Coating

Because catheter 50 (including tip 52) and introducer 120 are inserted into the uterus, a risk of infection may arise. Accordingly, an anti-bacterial coating can be applied on the entire disposable portion of intrauterine pressure catheter system 10. Such a coating provides an antiseptic surface active against major nosocomial pathogens. For example, a chlorhexidine and silver sulfadiazine coating can be molecularly bonded to the surface of catheter 50, the affixed tip 52, and introducer 120 (most of the disposable components of system 10).

VI. Connector Assembly

Figure 24:
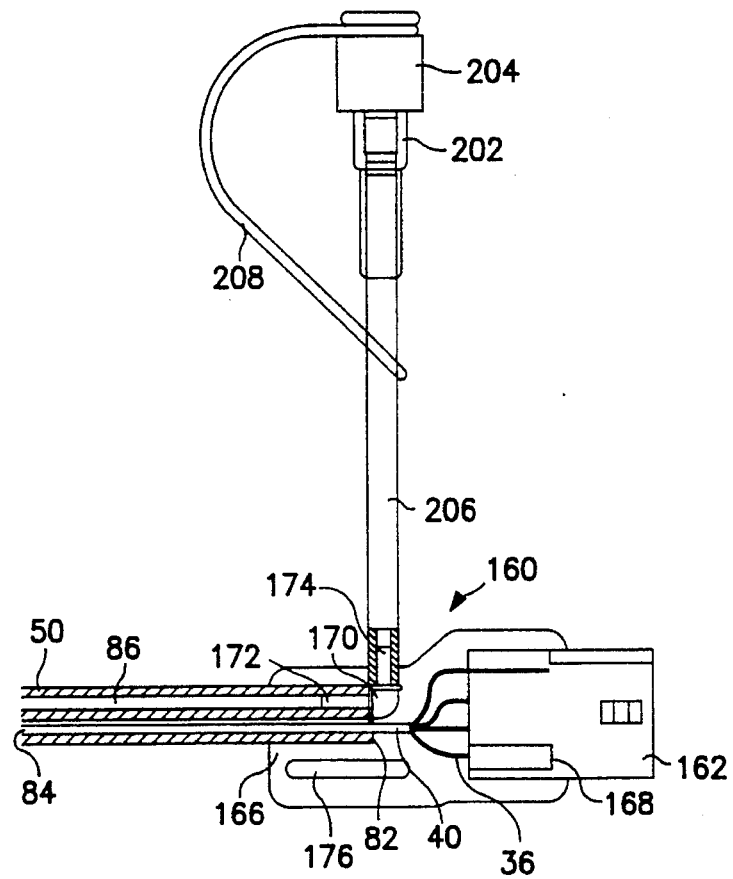
FIG. 24 is a partial cross-sectional view of the interconnection between the catheter, the luer fitting, and the female connector socket of the connector assembly in accordance with the present invention.

Connector assembly 160 has two main components, female connector socket 162 and male connector plug 164, as shown in FIG. 1. FIG. 24 is a partial cross-sectional view of the interconnection between catheter 50, luer fitting 200, and female connector socket 162 of connector assembly 160 in accordance with the present invention. As discussed above, second end 82 of catheter 50 is joined to connector assembly 160 at female connector socket 162. Specifically, catheter 50 is bonded to the body 166 enclosing female connector socket 162 using an adhesive. Leadwire cable 40 from sensor 20 travels through cable lumen 84 and ends in female connector socket 162 of connector assembly 160. Leadwire cable 40 is a bundle of four wires 36 connected on one end to connector pins 30 of sensor 20 and on the opposite end to the sockets 168 of female connector socket 162 of connector assembly 160.

Amnio lumen 86 from catheter 50 ends in an elbow tube fitting 170 having first arm 172 and second arm 174. Specifically, amnio lumen 86 engages first arm 172 of elbow tube fitting 170. Second arm 174 of elbow tube fitting 170 engages luer fitting 200. Elbow tube fitting 170 is made of a plastic such as nylon. A flexible elastomer such as silicon rubber or thermoplastic rubber is molded around the assembled components (cable 40 with wires 36, catheter 50, female connector socket 162, elbow tube fitting 170, and luer fitting 200) to form body 166.

Figure 26:
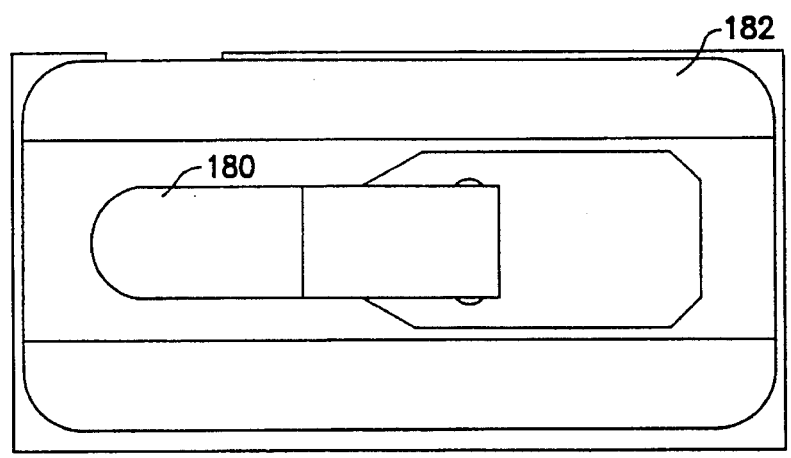
FIG. 26 is a top view of the adhesive attachment pad with the attachment strap attached in accordance with the present invention.

Body 166 of connector assembly 160 is affixed to the mother (typically, to the thigh or abdomen of the mother) using an attachment strap 180 (see FIGS. 1 and 26). Attachment strap 180 slips through attachment loop 176 formed in body 166. Attachment strap 180 may have "hook" material on one side and "loop" material on its opposite side (commercially available as Velcro™ material) to affix attachment strap 180 around the thigh.

Figure 25:
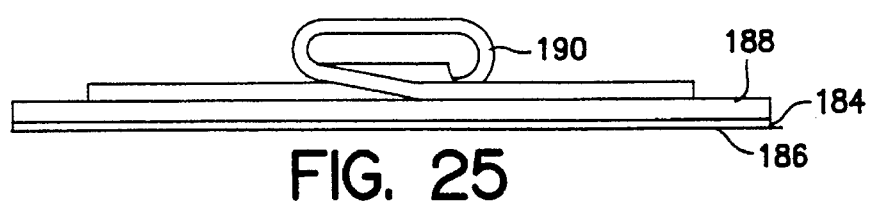
FIG. 25 is a side view of the adhesive attachment pad in accordance with the present invention.

Alternatively, as shown in FIGS. 1, 25, and 26, adhesive attachment pad 182 may be provided. Adhesive attachment pad 182 has an adhesive surface 184 covered by a protective liner 186. When liner 186 is removed, adhesive attachment pad 182 can be secured to the skin of the mother by pressing adhesive surface 184 against the skin. The top surface 188 of adhesive attachment pad 182, which lies over adhesive surface 184, may have "loop" material to engage the "hook" material on attachment strap 180 or a buckle 190 through which attachment strap 180 can be slipped. In either case, body 166 of connector assembly 160 and the components attached to body 166 (cable 40 with wires 36, catheter 50, female connector socket 162, elbow tube fitting 170, and luer fitting 200) are held fast to the mother's thigh or abdomen.

VII. Luer Fitting

Luer fitting 200 has three main components, a female luer lock fitting 202, a tethered male luer cap 204, and a luer tubing 206, as shown in FIG. 24. Male luer cap 204 is made of molded plastic such as polyethylene and may be colored for identification purposes. A tether 208 is affixed to male luer cap 204 and to luer tubing 206 so that, when male luer cap 204 is removed from female luer lock fitting 202, male luer cap 204 will not be lost. Tether 208 may be made of polyvinylchloride. Male luer cap 204 has internal threads which engage external threads on female luer lock fitting 202. The mating threads allow male luer cap 204 to be screwed on and off female luer lock fitting 202. Female luer lock fitting 202 is made of a clear material such as Eastman Ektar copolyester.

Luer tubing 206 runs from second arm 174 of elbow tube fitting 170 to female luer lock fitting 202. Thus, luer fitting 200 provides direct communication to amnio lumen 86 and, through amnio lumen 86, into the amniotic sac. When amnio lumen 86 is not in use, male luer cap 204 should be screwed in place on female luer lock fitting 202 to prevent fluid leakage. Infusion may be performed in a number of known ways. For example, a pre-filled syringe may be connected to female luer lock fitting 202 (with male luer cap 204 removed from female luer lock fitting 202 and retained by tether 208 on luer tubing 206) and tightened to prevent leakage. Then the fluid is injected. Alternatively, an IV solution bag may be connected to female luer lock fitting 202. Once fluid infusion is complete, the syringe or IV is disconnected from female luer lock fitting 202 and male luer cap 204 is replaced on female luer lock fitting 202.

VIII. Reusable Monitor Cable

A reusable monitor cable 220 is illustrated in FIG. 1. Monitor cable 220 has, on one end, male connector plug 164 of connector assembly 160. A monitor pin connector 264 is located on the opposite end of monitor cable 220. Connection of female connector socket 162 to male connector plug 164 gives an audible "click" assuring the user that electrical connection has been made and that connector assembly 160 is fully engaged. Monitor pin connector 264 mates with an external monitor or display 230. Once male connector plug 164 of monitor cable 220 has engaged female connector socket 162 to integrate connector assembly 160 and monitor pin connector 264 has mated with external monitor 230, the electrical signal path between sensor 20 and monitor 230 is complete.

IX. Test Member

Although not required, the ability to test monitor cable 220, male connector plug 164, and monitor pin connector 264 is desirable. Accordingly, reusable monitor cable 220 also incorporates a test member 240 allowing the user to assure that monitor cable 220, male connector plug 164, and monitor pin connector 264 are operational. As shown in FIG. 1, test member 240 is positioned about six inches (15 cm) from monitor pin connector 265 at the "dry" end of monitor cable 220 most removed from the wet environment of catheter 50. In addition, the location of test member 240 places it relatively close to monitor 230 so that the user can conveniently view and operate both test member 240 and monitor 230.

Figure 27:
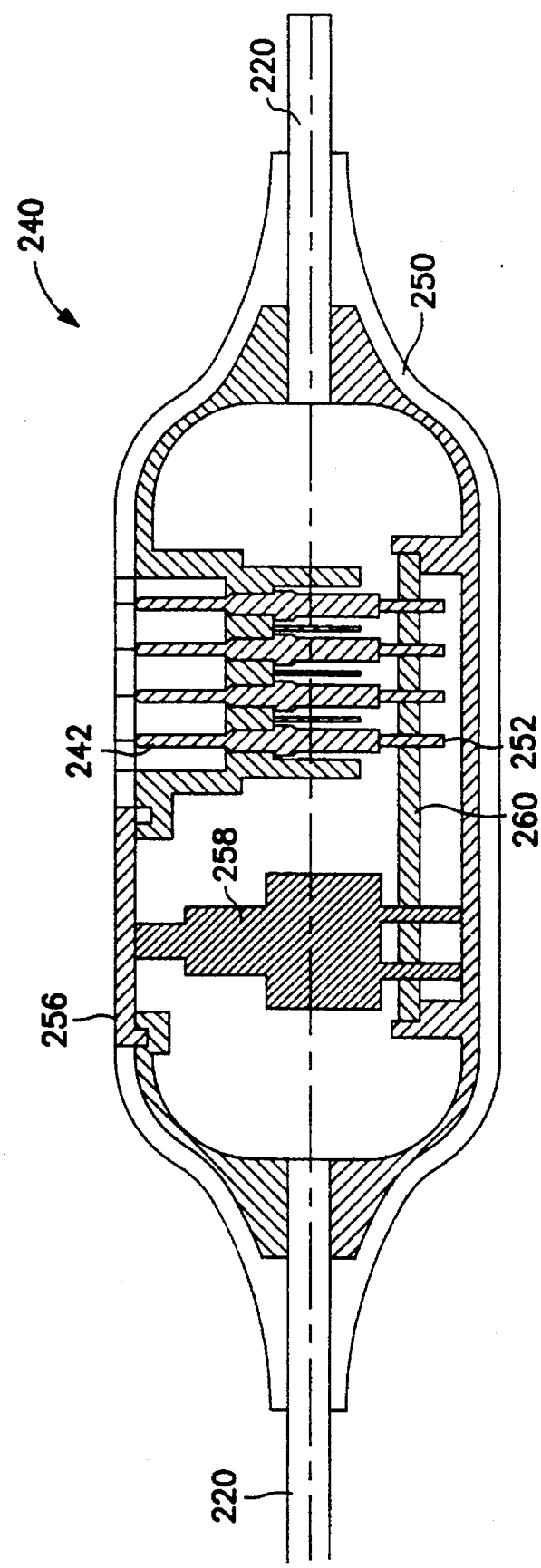
FIG. 27 is a cross section of the test member in accordance with the present invention.

FIG. 27 is a cross section of test member 240. Inside its housing 250, test member 240 has female terminals 242 which, like female connector socket 162, are designed to engage male connector plug 164. Female terminals 242 have extensions 252 which engage a PC board 260. When intrauterine pressure catheter system 10 is in use, and test member 240 is idle, a cover 244 is placed over female terminals 242. Pins 246 of cover 244 are inserted into female terminals 242. Cover 244 protects female terminals 242 from damage and residual contamination.

When the user desires to check monitor cable 220, male connector plug 164, and monitor pin connector 264, cover 244 is removed from test member 240. A tether 248 connects cover 244 with test member 240 and assures that cover 244 will not be lost. Access to female terminals 242 of test member 240 is now possible and male connector plug 164 is secured to female terminals 242. Monitor 230 will show whether monitor cable 220, male connector plug 164, and monitor pin connector 264 are working or not.

Figure 28:
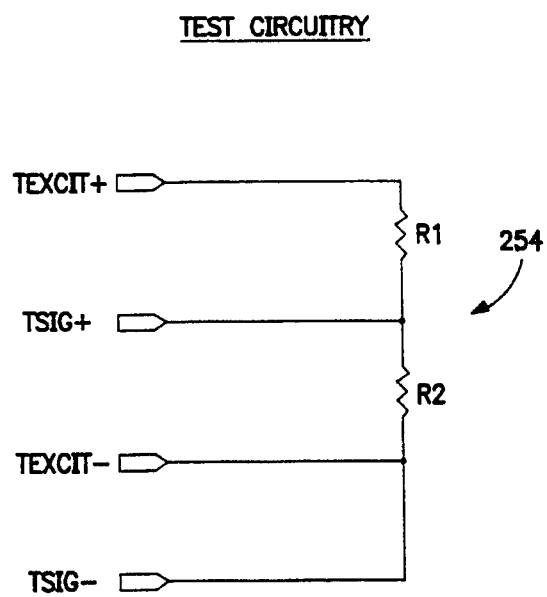
FIG. 28 is a circuit diagram of the test circuitry incorporated in the test member shown in FIG. 27.

The test circuitry 254 incorporated in test member 240 is shown in FIG. 28. Test circuitry 254 is a simple voltage divider network. Included in test circuitry 254 are a first resistor, R1, which may be a 110,000 ohm, 1/10 watt resistor, and a second resistor, R2, which may be a 27.4 ohm, 1/10 watt resistor. When male connector plug 164 is secured to female terminals 242 and test circuitry 254 is activated, monitor 230 will read approximately 50 mmHg if monitor 230, monitor cable 220, male connector plug 164, and monitor pin connector 264 are working. The reading may be between about 40–60 mmHg depending upon how monitor 230 has been zeroed.

Often, should intrauterine pressure catheter system 10 fail to function properly, the user might incorrectly assume that monitor 230, monitor cable 220, male connector plug 164, or monitor pin connector 264 are faulty and discard those components unnecessarily. Test member 240 provides the user with immediate assurance that the malfunction lies other than in the tested components. In addition, test member 240 may be used even absent a failure of system 10 to give the user more confidence in intrauterine pressure catheter system 10.

X. "Zero" Procedure

Before intrauterine pressure catheter system 10 and, specifically, sensor 20 having a pressure transducer can be used, sensor 20 should be balanced with monitor 230 to ensure that the readings monitor 230 produces are accurate. A pressure transducer is balanced to establish a specific pressure as the baseline or zero point from which the uterine pressure is measured. Thus, the zeroing procedure establishes a "zero" baseline or resting tone pressure for sensor 20.

As with any sensor, balancing of sensor 20 is a fundamental requirement and could be accomplished, in principle, at any pressure. Ambient or atmospheric pressure is preferred, however, at which the relative pressure to be measured is zero (hence, "zero setting"). To calibrate sensor 20, the ambient pressure is taken as the reference pressure and the difference from the measured pressure taken by sensor 20 is adjusted to zero.

The user can initially zero sensor 20 before inserting catheter 50. Even without taking catheter 50 from its sterilized packaging, sensor 20 will be exposed to atmospheric pressure on both sides of the transducer diaphragm. Accordingly, monitor 230 should indicate a zero value. If not, the user, following the instructions of the manufacturer of monitor 230, can set monitor 230 to a zero value. This procedure establishes a zero baseline for system 10.

Advances in technology have created pressure sensors that are extremely accurate and reliable. Nevertheless, the ability to check the electrical zero of system 10 remains important even after catheter 50 carrying sensor 20 has been inserted. In certain medical situations, such as abruptio placentia and toxemia of pregnancy, the tomis of the uterine contractions may be higher than normal. This provides an early indication of an abnormal medical situation. When unusual pressure readings are made by monitor 230, therefore, it is important to determine if they are caused by actual, biological changes or by electrical malfunctions. When the electrical zero of system 10 is checked and system 10 is closed, any pressure readings are caused by biological changes. In contrast, without a way to check the electrical performance of system 10, it would not be possible to determine the source of the unusual pressure readings.

Accordingly, system 10 includes structure to "zero" system 10 after insertion. Test member 240 includes a push button 256 which, when depressed, actuates a zero switch 258. These components are illustrated in FIG. 27. Zero switch 258 is part of the zero circuitry 270 detailed in FIG. 29.

Figure 29:
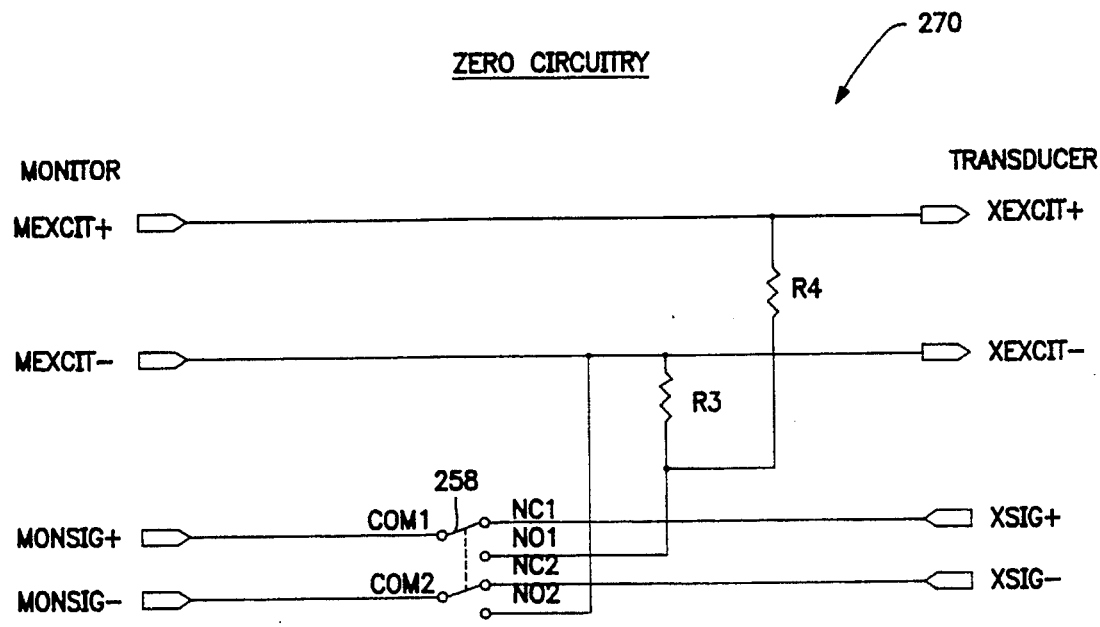
FIG. 29 is a circuit diagram of the zero circuitry incorporated in the test member shown in FIG. 27.

As illustrated in FIG. 29, zero circuitry 270 is not actuated (i.e., push button 256 is not depressed). Zero switch 258 is in the normally closed positions "NC1" and "NC2." Thus, the electrical paths of wires 36 (four are shown) comprising leadwire cable 40 from the transducer of sensor 20 to monitor 230 are unencumbered by resistors. Accordingly, the electrical signal of sensor 20 is read directly by monitor 230.

When the user desires to "zero" system 10, the signal from sensor 20 is cut so that the input signal from sensor 20 would be a null or zero output voltage. Alternatively, female connector socket 162 and male connector plug 164 of connector assembly 160 could be disengaged. This would remove sensor 20 from zero circuitry 270. In either case, push button 256 is depressed. That action flips zero switch 258 from the "NC1" and "NC2" positions to the normally open positions "NO1" and "NO2." Now zero circuitry 270 forms a simple voltage divider network including a third resistor, R3, which may be a 30.1 ohm, 1/10 watt resistor, and a fourth resistor, R4, which may be a 1 megohm, 1/10 watt resistor. The value read and displayed by monitor 230 should now be defined by the pre-determined resistance in zero circuitry 270, preferably set to be the designed offset of the transducer as received from the manufacturer (typically, a negligible amount such as 8 mmHg). If so, the user can adjust monitor 230 to yield a zero reading. Push button 256 is depressed and held while monitor 230 is adjusted.

Zero switch 258 and zero circuitry 270 could be placed on female connector socket 162. Because both monitor 230 and sensor 20 must be zeroed, the advantage of placing zero switch 258 and zero circuitry 270 on female connector socket 162 is that monitor 230 and sensor 20 can be zeroed simultaneously. The drawback is, however, that female connector socket 162—otherwise available as a conventional, off-the-shelf component—becomes expensive. The expense is exacerbated because female connector socket 162 is part of the disposable catheter 50 and placement of zero switch 258 and zero circuitry 270 on female connector socket 162 unnecessarily increases the cost and complexity of a disposable component.

Preferably, therefore, zero switch 258 and zero circuitry 270 are incorporated as a component of reusable monitor cable 220. Zero switch 258 and zero circuitry 270 could be placed either on monitor pin connector 264 or on male connector plug 164. The advantage of such placement is that monitor cable 220, with both monitor pin connector 264 and male connector plug 164, is reusable and better justifies the added expense of zero switch 258 and zero circuitry 270. The disadvantage of such placement is, however, that monitor pin connector 264 and male connector plug 164—which are otherwise available as conventional, off-the-shelf components—must be redesigned to incorporate zero switch 258 and zero circuitry 270.

For these reasons, zero switch 258 and zero circuitry 270 are incorporated in test member 240. Test member 240 is a specially designed component anyway and can easily be designed to include zero switch 258 and zero circuitry 270. Because test member 240 is part of monitor cable 220, such a design advantageously incorporates zero switch 258 and zero circuitry 270 as part of reusable monitor cable 220.

Although test member 240 with zero switch 258 and zero circuitry 270 can be used to zero monitor 230, sensor 20 itself will not be zeroed. The reliability and accuracy of conventional pressure transducer sensors generally render it unnecessary to zero sensor 20 in use after sensor 20 has been zeroed against monitor 230 before insertion and use. Nevertheless, some incremental accuracy and, perhaps more important, some increased user confidence can be obtained by zeroing sensor 20 in use. After the transducer of sensor 20 has been balanced initially, therefore, it may be desirable to calibrate system 10 during use to compensate for electrical inaccuracies in the transducer.

In order to calibrate system 10, a known pressure must be applied to the transducer diaphragm of sensor 20 so that monitor 230 can be calibrated to that pressure. Vent hole 88 and cable lumen 84 normally function to provide atmospheric pressure to one side of the diaphragm of the pressure transducer of sensor 20. The atmospheric pressure provided by vent hole 88 and cable lumen 84 could also be used to zero or calibrate sensor 20—even when sensor 20 is inside the uterus.

The side of transducer diaphragm opposite the atmospheric pressure normally is exposed to uterine pressure when positioned in the uterus. Such exposure could be cut off and the atmospheric pressure—provided by vent hole 88 and cable lumen 84 or, alternatively, by third lumen 94—could be directed to both sides of the transducer diaphragm. A silicon microvalve might be incorporated into catheter tip 52 to perform these functions. Monitor 230 should then display a zero reading. If not, the electrical zero can be adjusted. Then the transducer diaphragm is exposed again to the uterine pressure to be monitored.

Similarly, vent hole 88 and cable lumen 84 (or third lumen 94) can be used (with a silicon microvalve) to direct a known pressure source to the side of the diaphragm opposite atmospheric pressure. If monitor 230 and sensor 20 are operational and calibrated properly, monitor 230 should display a pressure value equal to that of the known pressure source. Alternatively, a vacuum could be imposed through cable lumen 84 via vent hole 88 to the backside of the transducer diaphragm. The transducer is a true differential device. Therefore, a vacuum on the backside of the diaphragm is completely equivalent to a pressure on the uterus side of the diaphragm.

XI. Use of the System

Intrauterine catheter system 10 is used as follows. External monitor 230 is turned on. Monitor pin connector 264 is plugged into monitor 230. If desired, test member 240 can be used to assure that monitor cable 220, male connector plug 164, and monitor pin connector 264 are operational. Monitor 230 is then zeroed by pushing zero button 256 on test member 240. Monitor cable 220 is connected, via male connector plug 164, to female connector socket 162 and connector assembly 160 is completed.

The user is now ready to insert catheter 50. Introducer 120 slides over catheter 50 until introducer 120 is adjacent catheter tip 52. Catheter 50 is then inserted using introducer 120 by gently sliding catheter tip 52 through the cervical os and into the amniotic space. First and second position indicators 96 and 98 on catheter 50 indicate insertion depths of 12 and 18 inches (30 cm and 45 cm), respectively, relative to the introitus. Catheter 50 is advanced until second position indicator 98, the 18 inch (45 cm) mark, is at the introitus. Second position indicator 98 indicates that catheter tip 52 has progressed about 12–14 inches (30–35 cm) into the uterus and should be positioned at the fundus of the uterus.

Holding introducer 120 in one hand and catheter 50 in the other, introducer 120 is retracted and separated from catheter 50. Adhesive attachment pad 182 is applied to the mother's thigh or abdomen and attachment strap 180 is secured to adhesive attachment pad 182. Attachment strap 180 is adjusted as desired for patient comfort. Intrauterine pressure catheter system 10 can be re-zeroed during use.

To implement the fluid infusion procedure, male luer cap 204 is removed from female luer lock fitting 202 on luer tubing 206. A prefilled infusion syringe is connected directly to female luer lock fitting 202 and tightened adequately to prevent leakage. The fluid is injected from the syringe. When fluid infusion is complete, the syringe is disconnected and male luer cap 204 is tightened onto female luer lock fitting 202.

Although illustrated and described herein with reference to certain specific embodiments, the present invention is nevertheless not intended to be limited to the details shown. Rather, various modifications may be made in the details within the scope and range of equivalents of the claims and without departing from the spirit of the invention. For example, although particularly adapted to measure intrauterine pressure, system 10 could be used to measure a wide variety of intracavity pressures. Intra-articular, esophageal, intra-intestinal, and intra-cranial pressures, among others, could be monitored using system 10.

What is claimed is:

1. An intrauterine pressure catheter system for measuring the pressure in the uterus of a woman in labor and delivering a signal representative of intrauterine pressure to an external monitor, said system comprising:

a disposable, firm, flexible catheter having:

(a) a first end, (b) a second end, (c) a cable lumen longitudinally traversing the inside of said catheter from said first end to said second end with a vent hole emanating from said cable lumen proximate said second end of said catheter, and (d) an amnio lumen longitudinally traversing the inside of said catheter from said first end to said second end with at least one amnio port emanating from said amnio lumen proximate said first end of said catheter;

a disposable, asymmetric tip affixed to said first end of said catheter with an undercut resisting slippage of said catheter following insertion into the uterus, said tip having a width greater than its height and tapering to an apex opposite said first end of said catheter;

a disposable pressure sensor fixed and rigidly mounted in said tip affixed to said catheter, said pressure sensor measuring intrauterine pressure;

a disposable first connector affixed to said second end of said catheter;

a disposable leadwire cable carried in said cable lumen of said catheter and electrically connecting said pressure sensor to said first connector; and a reusable monitor cable having a first end, a second end, a second connector on said first end of said monitor cable adapted to engage said first connector, and a monitor connector on said second end of said monitor cable adapted to engage the monitor, said monitor cable transmitting electrical signals from said first connector to the monitor.

2. A system according to claim 1 further comprising a disposable introducer engaging and manipulating said catheter, said introducer having:

(a) a bottom with a thickness and a longitudinal slot disposed along the entire length of said bottom, (b) a top with a thickness greater than the thickness of said bottom, (c) a pair of side walls each with a thickness that transitions between the thickness of said top and the thickness of said bottom, said introducer defining a C-shaped cross section.

3. A system according to claim 1 further comprising a test member on said monitor cable proximate said monitor connector, said test member including terminals adapted to engage said second connector and test circuitry adapted to assure that said monitor cable, said second connector, and said monitor connector are operational.

4. A system according to claim 1 wherein said tip is a soft elastomer.

5. A system according to claim 1 wherein said tip has a maximum height of about 0.5 cm and tapers to said apex of said tip—at which the height is zero—over a distance of about 1.0 cm, is about 1.1 cm at its widest point and tapers to said apex of said tip—at which the width is zero—over a distance of between 1.0 and 1.2 cm, and is about 3.3 cm long.

6. A system according to claim 1 wherein said sensor has:

(a) a housing with a top surface;

(b) an armature within said housing having a rear surface;

(c) a miniature silicon diaphragm pressure transducer fixedly mounted on said armature;

(d) an orifice protruding from said top surface of said housing;

(e) a silicon gel filling said orifice;

(f) a port on said rear surface of said armature fitting tightly within said cable lumen of said catheter, said leadwire cable traveling away from said sensor through said port of said armature and into said cable lumen; and (g) a solid plug on said rear surface of said armature fitting tightly within said amnio lumen of said catheter, said solid plug stopping said amnio lumen.

7. A system according to claim 6 wherein said tip has a top surface and said orifice of said sensor is recessed within said top surface of said tip.

8. A system according to claim 1 wherein said catheter has a hardness between 80 and 98 Shore A.

9. A system according to claim 1 wherein said catheter has a handle with a flared region located on said catheter between said first end and said second end so that said flared region is at the introitus area of the mother when said catheter is fully inserted into the uterus.

10. A system according to claim 1 wherein said catheter is a thermoplastic elastomer having a length of about 75 cm, a width of about 0.67 cm, and a height of about 0.38 cm.

11. A system according to claim 1 further comprising an anti-bacterial coating bonded to said catheter and said tip affixed to said catheter.

12. A system according to claim 11 wherein said coating is chlorhexidine and silver sulfadiazine.

13. A system according to claim 1 further comprising a disposable luer fitting communicating with said amnio lumen of said catheter and providing direct communication, through said amnio lumen, into the uterus.

14. A system according to claim 13 wherein said luer fitting has a luer tubing with a first end and a second end, said luer tubing communicating with said amnio lumen of said catheter on said first end of said luer tubing; a female luer lock fitting engaging said second end of said luer tubing; and a male luer cap tethered to said luer tubing and adapted to engage said female luer lock fitting.

15. A system according to claim 13 further comprising an elbow having a first arm and a second arm, said elbow disposed between said catheter and said luer fitting, said first arm of said elbow engaging said amnio lumen of said catheter and said second arm of said elbow engaging said luer tubing.

16. A disposable, asymmetric tip adapted to be affixed to a catheter to be inserted into the cavity of a patient, said tip comprising:

an undercut resisting slippage of said tip and the catheter following insertion of said tip and the catheter into the cavity;

a height tapering to an apex opposite the catheter;

a width greater than said height and tapering to said apex opposite the catheter; and a length.

17. A tip according to claim 16 wherein said tip is a soft elastomer.

18. A tip according to claim 16 wherein said height is a maximum of about 0.5 cm and tapers to said apex of said tip—at which said height is zero—over a distance of about 1.0 cm, said width is a maximum of about 1.1 cm and tapers to said apex of said tip—at which said width is zero—over a distance of between 1.0 and 1.2 cm, and said length is about 3.3 cm.

19. A tip according to claim 16 further comprising an anti-bacterial coating bonded to said tip.

20. An intrauterine pressure catheter system for measuring the pressure in the uterus of a woman in labor and delivering a signal representative of intrauterine pressure to an external monitor, said system comprising:

a disposable, firm, flexible catheter having:
(a) a first end,
(b) a second end,
(c) a cable lumen longitudinally traversing the inside of said catheter from said first end to said second end with a vent hole emanating from said cable lumen proximate said second end of said catheter, and
(d) an amnio lumen longitudinally traversing the inside of said catheter from said first end to said second end with at least one amnio port emanating from said amnio lumen proximate said first end of said catheter;

a disposable tip affixed to said first end of said catheter;

a disposable introducer engaging and manipulating said catheter, said introducer having:
(a) a bottom with a thickness and a longitudinal slot disposed along the entire length of said bottom,
(b) a top with a thickness greater than the thickness of said bottom,
(c) a pair of side walls each with a thickness that transitions between the thickness of said top and the thickness of said bottom, said introducer defining a C-shaped cross section;

a disposable pressure sensor fixed and rigidly mounted in said tip affixed to said catheter, said pressure sensor measuring intrauterine pressure;

a disposable first connector affixed to said second end of said catheter;

a disposable leadwire cable carried in said cable lumen of said catheter and electrically connecting said pressure sensor to said first connector; and a reusable monitor cable having a first end, a second end, a second connector on said first end of said monitor cable adapted to engage said first connector, and a monitor connector on said second end of said monitor cable adapted to engage the monitor, said monitor cable transmitting electrical signals from said first connector to the monitor.

21. A system according to claim 20 further comprising a test member on said monitor cable proximate said monitor connector, said test member including terminals adapted to engage said second connector and test circuitry adapted to assure that said monitor cable, said second connector, and said monitor connector are operational.

22. A system according to claim 21 wherein said test member has:
(a) zero circuitry including a zero switch with a first position directing the electrical signal from said sensor to the monitor and a second position forming a voltage divider network with two resistors, and
(b) a push button actuating said zero switch.

23. A system according to claim 20 further comprising an anti-bacterial coating bonded to said introducer.

24. A system according to claim 23 wherein said coating is chlorhexidine and silver sulfadiazine.

25. A system according to claim 20 wherein said introducer is polyolefin.

26. A system according to claim 20 wherein said introducer has an open front end, an open back end, one of a chamfer and a radius on said top at said front end, a radius on said bottom at said front end, and blended radii on said pair of side walls at said front end.

27. A system according to claim 20 wherein said introducer has an elliptical cross section with a major axis approximating the height of said catheter and a minor axis approximating the width of said catheter.

28. A system according to claim 20 wherein said slot of said introducer is about 0.42 cm wide, said thickness of said top of said introducer is about 0.076 cm, and said thickness of said bottom of said introducer is about 0.020 inches.

29. A system according to claim 20 wherein said introducer has a grip.

30. An introducer adapted to engage and manipulate a catheter to be inserted into the cavity of a patient, said introducer comprising:
   a bottom with a thickness and a longitudinal slot disposed along the entire length of said bottom;
   a top with a thickness greater than the thickness of said bottom; and
   a pair of side walls each with a thickness that transitions between the thickness of said top and the thickness of said bottom, said introducer defining a C-shaped cross section.

31. An introducer according to claim 30 further comprising an anti-bacterial coating bonded to said introducer.

32. An introducer according to claim 30 wherein said introducer is polyolefin.

33. An introducer according to claim 30 wherein said introducer has an open front end, an open back end, one of a chamfer and a radius on said top at said front end, a radius on said bottom at said front end, and blended radii on said pair of side walls at said front end.

34. An introducer according to claim 30 wherein said introducer has an elliptical cross section with a major axis approximating the height of the catheter and a minor axis approximating the width of the catheter.

35. An introducer according to claim 30 wherein said slot of said introducer is about 0.42 cm wide, said thickness of said top of said introducer is about 0.076 cm, and said thickness of said bottom of said introducer is about 0.020 inches.

36. An introducer according to claim 30 wherein said introducer has a grip.

37. An intrauterine pressure catheter system for measuring the pressure in the uterus of a woman in labor and delivering a signal representative of intrauterine pressure to an external monitor, said system comprising:
   a disposable, firm, flexible catheter having:
      (a) a first end,
      (b) a second end,
      (c) a cable lumen longitudinally traversing the inside of said catheter from said first end to said second end with a vent hole emanating from said cable lumen proximate said second end of said catheter, and
      (d) an amnio lumen longitudinally traversing the inside of said catheter from said first end to said second end with at least one amnio port emanating from said amnio lumen proximate said first end of said catheter;
   a disposable tip affixed to said first end of said catheter;
   a disposable pressure sensor fixed and rigidly mounted in said tip affixed to said catheter, said pressure sensor measuring intrauterine pressure;
   a disposable first connector affixed to said second end of said catheter;
   a disposable leadwire cable carried in said cable lumen of said catheter and electrically connecting said pressure sensor to said first connector; and
   a reusable monitor cable having:
      (a) a first end,
      (b) a second end,
      (c) a second connector on said first end of said monitor cable adapted to engage said first connector,
      (d) a monitor connector on said second end of said monitor cable adapted to engage the monitor, said monitor cable transmitting electrical signals from said first connector to the monitor, and
      (e) a test member on said monitor cable proximate said monitor connector, said test member including terminals adapted to engage said second connector and test circuitry adapted to assure that said monitor cable, said second connector, and said monitor connector are operational.

38. A system according to claim 37 further comprising an anti-bacterial coating bonded to said catheter, said tip affixed to said catheter, and said introducer.

39. A system according to claim 38 wherein said coating is chlorhexidine and silver sulfadiazine.

40. A system according to claim 37 wherein said test member has a cover adapted to engage said terminals when said test member is inactive.

41. A system according to claim 37 wherein said test circuitry has a 110,000 ohm, 1/10 watt resistor and a 27.4 ohm, 1/10 watt resistor.

42. A system according to claim 37 wherein said test member has:
   (a) zero circuitry including a zero switch with a first position directing the electrical signal from said sensor to said monitor and a second position forming a voltage divider network with two resistors, and
   (b) a push button actuating said zero switch.

43. A system according to claim 42 wherein said resistors of said zero circuitry are a 30.1 ohm, 1/10 watt resistor and a 1 megohm, 1/10 watt resistor.

44. An intrauterine pressure catheter system for measuring the pressure in the uterus of a woman in labor and delivering a signal representative of intrauterine pressure to an external monitor, said system comprising:
   a disposable, firm, flexible catheter having:
      (a) a first end,
      (b) a second end,
      (c) a cable lumen longitudinally traversing the inside of said catheter from said first end to said second end with a vent hole emanating from said cable lumen proximate said second end of said catheter, and
      (d) an amnio lumen longitudinally traversing the inside of said catheter from said first end to said second end with at least one amnio port emanating from said amnio lumen proximate said first end of said catheter;
   a disposable, asymmetric tip affixed to said first end of said catheter with an undercut resisting slippage of said catheter following insertion into the uterus, said tip having a width greater than its height and tapering to an apex opposite said first end of said catheter;
   a disposable introducer engaging and manipulating said catheter, said introducer having:
      (a) a bottom with a thickness and a longitudinal slot disposed along the entire length of said bottom,
      (b) a top with a thickness greater than the thickness of said bottom,
      (c) a pair of side walls each with a thickness that transitions between the thickness of said top and the thickness of said bottom, said introducer defining a C-shaped cross section;
   a disposable pressure sensor fixed and rigidly mounted in said tip affixed to said catheter, said pressure sensor measuring intrauterine pressure;

a disposable first connector affixed to said second end of said catheter;

a disposable leadwire cable carried in said cable lumen of said catheter and electrically connecting said pressure sensor to said first connector; and a reusable monitor cable having:
(a) a first end,
(b) a second end,
(c) a second connector on said first end of said monitor cable adapted to engage said first connector,
(d) a monitor connector on said second end of said monitor cable adapted to engage said monitor, said monitor cable transmitting electrical signals from said first connector to said monitor, and
(e) a test member on said monitor cable proximate said monitor connector, said test member including terminals adapted to engage said second connector and test circuitry adapted to assure that said monitor cable, said second connector, and said monitor connector are operational.

* * * * *